US 7,435,833 B2

(12) United States Patent
Yeh et al.

(10) Patent No.: US 7,435,833 B2
(45) Date of Patent: Oct. 14, 2008

(54) INHIBITORS OF THE 11-BETA-HYDROXYSTEROID DEHYDROGENASE TYPE 1 ENZYME

(75) Inventors: Vince S. Yeh, Chicago, IL (US); Ravi Kurukulasuriya, Lake Forest, IL (US); David J. Madar, Miami Beach, FL (US); James T. Link, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/697,044

(22) Filed: Apr. 5, 2007

(65) Prior Publication Data

US 2008/0076819 A1     Mar. 27, 2008

Related U.S. Application Data

(60) Provisional application No. 60/790,141, filed on Apr. 7, 2006.

(51) Int. Cl.
*C07D 207/00*     (2006.01)
*C07D 403/00*     (2006.01)
*A61K 31/00*     (2006.01)

(52) U.S. Cl. .................. 548/518; 514/217.08; 540/602

(58) Field of Classification Search ................ 548/518; 514/217.08; 540/602
See application file for complete search history.

(56) References Cited

U.S. PATENT DOCUMENTS 4,324,791  A       4/1982  Welstead, Jr.
6,784,167  B2 *    8/2004  Wood et al. .................. 514/63

FOREIGN PATENT DOCUMENTS

| EP | 1 180 513 | 2/2002 |
|----|-----------|--------|
| WO | 03/059905 | 7/2003 |
| WO | 2004/089470 | 10/2004 |
| WO | 2005/108361 | 11/2005 |
| WO | 2006/104280 | 10/2006 |

OTHER PUBLICATIONS

Anstead, G.M., "Steroids, Retinoids, and Wound Healing", *Adv. Wound Care*, 11:277-285 (1998).
Armaly, M.F., "Dexamethasone Ocular Hypertension and Eosinopenia, and Glucose Tolerance Test", *Arch. Ophthalmol.*, 78:193-197 (1967).
Baxter, J.D., "Glucocorticoid Hormone Action", *Pharmac. Ther.*, 2:605-659 (1976).
Beer, H-D., et al., "Glucocorticoid-Regulated Gene Expression during Cutaneous Wound Repair", *Vitamins & Hormones*, 59:217-239 (2000).
Belanoff, J.K., et al., "Corticosteroids and cognition", *J. of Psych. Res.*, 35:127-145 (2001).
Bertagna, X., et al., "Cushing's Disease, *Cushing's Dis. In: Melmed S., Ed. The Pituitary*", 2nd Ed(Chapt. 13):592-612 (2002).

Billaudel, B., et al., "Direct Effect of Corticostrone upon Insuline Secretion Studied by Three Different Techniques", *Horm. Metabl. Res.*, 11:555-560 (1979).
Bland, R., et al., "Characterization of 11β-hydroxysteroid dehydrongenase activity and corticosteroid receptor expression in human osterosarcoma cell lines",*J. of Endocrin.*, 61:455-464 (1999).
Boscaro, M., et al., "Cushing's syndrome", *The Lancet*, 357:783-791 (2001).
Cooper, M.S., et al., "Expression and Functional Consequences of 11β-Hydroxysteroid Dehydrogenase Activity in Human Bone", *Bone*, 27(3):375-381 (2000).
Cooper, M.S., et al., "Osteoblastic 11β-Hydroxysteroid Dehydrogenase Type 1 Activity Increases With Age and Glucocorticoid Exposure",*J. of Bone & Mineral Res.*, 17(6):979-986 (2002).
Davani, B., "Type 1 11β-Hydroxysteroid Dehydrogenase Mediates Glucocorticoid Activation and Insulin Release in Pancreatic Islets", *J. of Biol. Chem.*, 275(45:334841-34844 (2000).
de Quervain, D. J.-F., et al., "Glucocorticoid-related genetic susceptibility for Alzheimer's disease", *Hum. Molec. Genetics*, 13(1):47-52 (2004).
Ilammami, M.M. & Siitteri, P.K., "Regulation of 1 1β-Hydroxysteroid Dehydrogenase Activity in Human Skin Fibroblasts: Enzymatic Modulation of Glucocorticoid Action",*J. of Clin. Endocrin & Metab.*, 73(2):326-334 (1991).
Hermanowski-Vosatka, A., et al., "11β-HSD1 inhibition ameliorates metabolic syndrome and prevents progression of atherosclerosis in mice",*J. of Exp. Med.*, 202(4):517-527 (2005).
Hodge, G., et al., "Salt-sensitive hypertension resulting from nitric oxide synthase inhibition is associated with loss of regulation of angiotensin II in the rat", *Exp. Physiol.*, 87:1-8 (2002).

(Continued)

*Primary Examiner*—Rita J Desai
*Assistant Examiner*—John Mabry
(74) *Attorney, Agent, or Firm*—Sreenivasarao Vepachedu

(57) ABSTRACT

A compound of formula (I):

$$\text{(I)}$$

or a pharmaceutically acceptable salt, prodrug, salt of a prodrug, or a combination thereof. Methods of inhibiting 11-beta-hydroxysteroid dehydrogenase Type 1 enzyme. Methods of treating non-insulin dependent type 2 diabetes, insulin resistance, obesity, lipid disorders, metabolic syndrome and other diseases and conditions that are mediated by excessive glucocorticoid action.

20 Claims, No Drawings

OTHER PUBLICATIONS

Issa, A.M., et al., "Hypothalamic-Pituitary-Adrenal Activity in Aged, Cognitively Impaired and Cognitively Unimpaired Rats",*J. of Neurosci.*, 10(10):3247-3254 (1990).

Jones, C.D., et al., "Effects of Substituent Modification on Face Selection in Reduction",*J. Org. Chem.*, 83(8):2758-2760 (1998).

Kolocouris, N., et al., "Synthesis an Antiviral Activity Evaluation of Some New Aminoadamantane Derivatives. 2", *J. Med. Chem.*, 39:3307-3318 (1996).

Kornel, L., et al., "Mechanism of the effects of glucocorticois and mineralocorticoids on vascular smooth muscle contractility", *Steriods*, 58:580-587 (1993).

Lupien, S.J., et al., "Cortisol levels during human aging predict hippocampal atrophy and memory deficits", *Nature Neurosci.*, 1(1):69-73 (1998).

Mason, D., "Genetic variation in the stress response: susceptibility to experimental allergic encephalomyelitis and implications for human inflammatory disease",*Immun. Today*, 12(2):57-60 (1991).

Masuzaki, H., et al., "A Transgenic Model of Fisceral Obesity and the Metabolic Syndrome",*Science*, 294:2166-2170 (2001).

Masuzaki, H., et al., "Transgenic amplification of glucocorticoid action in adipose tissue causes high blood pressure in mice", *J. of Clin. Invest.*, 112(1):83-90 (2003).

Montague, C.T. & O'Rahilly, S., "The Perils of Portliness: Causes and Consequences of Fisceral Adiposity", *Diabetes*, 49(6):883-888 (2000).

Morton, N.M., et al., "Improved Lipid and Lipoprotein Profile, Hepatic Insulin Sensitivity, and Glucose Tolerance in 11β-Hydroxysteroid Dehydrogenase Type 1 Null Mice",*J. of Biol. Chem.*, 276(44):41293-41500 (2001).

Orth, D.N., "Cushing's Syndrome",*Med. Prog.*, 332(12):791-803 (1995).

Ortsäter, H., et al., "Regulation of 11β-hydroxyteroid dehydrogenase type 1 and glucose-stimulated insulin secretion in pancreatic islets of Langerhans", *Diabetes Metab. Res. Rev.*, 21:359-366 (2005).

Paterson, J.M., et al., "Metabolic syndrome without obesity: Hepatic overexpression of 11β-hydroxysteroid dehydrogenase type 1 in transgenic mice",*Proc. Natl. Acad. Sci.*, 101(18):7088-7093 (2004).

Pirpiris, M., et al., Pressor responsiveness in corticosteroid-induced hypertension in humans, *Hypertension*, 19:567-574 (1992).

Rauz, S., et al., "Expression and Putative Role of 11β-Hydroxysteroid Dehydrogenase Isozymes within the Human Eye", *Invest. Ophthal. & Vis. Sci.*, 42(9):2037-2042 (2001).

Rauz, S., et al., "Inhibition of 11β-hydroxysteroid dehydrogenase type 1 lowers intraocular pressure in patients with ocular hypertension", *Q. J. Med.*, 96:481-490 (2003).

Rehman, Q. & Lane, N.E., "Effect of Glucocorticoids on Bone Density",*Med. Pediatr. Oncol.*, 41:212-216 (2003).

Rook, G.A., "Glucocorticoids and immune function",*Baillier's Clin. Endocrinol. Metab.*, 13:576-581 (1999).

Schteingart, D.E., "Cushing Syndrome",*Princ. & Prac. Of Endoc. & Metab.*, Chapt. 75:723-728 (2001).

Small, G.R., et al., "Preventing local regeneration of glucocorticoids by 11β-hydroxysteroid dehydrogenase type 1 enhances angiogenesis",*Proc. Natl. Acad. Sci.*, 102(34):12165-12170 (2005).

Stokes, J., et al., "Altered Peripheral Sensitivity to Glucocorticoids in Primary Open-Angle Glaucome", *Invest. Ophthalmol. Vis. Sci.*, 44:5163-5167 (2003).

Tronche, F., et al., "Disruption of the glucocorticoid receptor gene in the nervous system results in reduced anxiety", *Nature Genetics*, 23:99-103 (1999).

Turner, R.T., et al., "Prednisone Inhibits Formation of Cortical Bone in Sham-Operated and Ovarictomized Female Rats", *Calcif. Tissue Int.*, 56:311-315 (1995).

Walker, B.R. & Williams, B.C., "Corticosteroids and vascular tone: mapping the messenger maze",*Clin. Sci.*, 82:597-605 (1992).

Walker, B.R., et al., "Carbenoxolone Increases Hepatic Insulin Sensitivity in Man; A Novel Role for 11-Oxosteroid Reductase in Enhancing Glucocorticoid Receptor Activation",*J. of Clin. Endocrin. & Metab.*, 80(11):3155-3159 (1995).

Wolkowitz, O.M., et al., "The "Steroid Dementia Syndrome" An Unrecognized Complication of Glucocorticoid Treatment", *Ann. NY Acad. Sci.*, 1032:191-194 (2004).

Yau, J.L.W., et al., "Lack of tissue glucocorticoid reactivation in 11β-hydroxysteroid dehydrogenase type 1 knockout mice ameliorates age-related learning impairments", *Proc. Natl. Acad. Sci.*, 98(8):4716-4721 (2001).

Yeh, V.S.C., et al., "A Highly Efficient Synthesis of Potent and Selective Butyrolactam Inhibitors of 1 β-Hsd1", *Org. Ltrs.*, 8(18):3963-3966 (2006).

\* cited by examiner

INHIBITORS OF THE 11-BETA-HYDROXYSTEROID DEHYDROGENASE TYPE 1 ENZYME

This application claims priority from U.S. Provisional Patent Application Ser. No. 60/790,141, filed Apr. 7, 2006, incorporated herein by reference.

FIELD OF INVENTION

The present invention relates to compounds that are enzyme inhibitors, and more specifically inhibitors of the 11-beta-hydroxysteroid dehydrogenase Type 1 enzyme.

BACKGROUND OF THE INVENTION

Insulin is a hormone that modulates glucose and lipid metabolism. Impaired action of insulin (i.e., insulin resistance) results in reduced insulin-induced glucose uptake, oxidation and storage, reduced insulin-dependent suppression of fatty acid release from adipose tissue (i.e., lipolysis), and reduced insulin-mediated suppression of hepatic glucose production and secretion. Insulin resistance frequently occurs in diseases that lead to increased and premature morbidity and mortality.

Diabetes mellitus is characterized by an elevation of plasma glucose levels (hyperglycemia) in the fasting state or after administration of glucose during a glucose tolerance test. While this disease can be caused by several underlying factors, it is generally grouped into two categories, Type 1 and Type 2 diabetes. Type 1 diabetes, also referred to as Insulin Dependent Diabetes Mellitus ("IDDM"), is caused by a reduction of production and secretion of insulin. In Type 2 diabetes, also referred to as non-insulin dependent diabetes mellitus ("NIDDM"), insulin resistance is a significant pathogenic factor in the development of hyperglycemia. Typically, the insulin levels in Type 2 diabetes patients are elevated (i.e., hyperinsulinemia), but this compensatory increase is not sufficient to overcome the insulin resistance. Persistent or uncontrolled hyperglycemia in both Type 1 and Type 2 diabetes mellitus is associated with increased incidence of macrovascular and/or microvascular complications including atherosclerosis, coronary heart disease, peripheral vascular disease, stroke, nephropathy, neuropathy, and retinopathy.

Insulin resistance, even in the absence of profound hyperglycemia, is a component of the metabolic syndrome. Recently, diagnostic criteria for metabolic syndrome have been established. To qualify a patient as having metabolic syndrome, three out of the five following criteria must be met: elevated blood pressure above 130/85 mmHg, fasting blood glucose above 110 mg/dl, abdominal obesity above 40" (men) or 35" (women) waist circumference, and blood lipid changes as defined by an increase in triglycerides above 150 mg/dl or decreased HDL cholesterol below 40 mg/dl (men) or 50 mg/dl (women). It is currently estimated that 50 million adults, in the US alone, fulfill these criteria. That population, whether or not they develop overt diabetes mellitus, are at increased risk of developing the macrovascular and microvascular complications of Type 2 diabetes listed above.

Available treatments for Type 2 diabetes have recognized limitations. Diet and physical exercise can have profound beneficial effects in Type 2 diabetes patients, but compliance is poor. Even in patients having good compliance, other forms of therapy can be required to further improve glucose and lipid metabolism.

One therapeutic strategy is to increase insulin levels to overcome insulin resistance. This can be achieved through direct injection of insulin or through stimulation of the endogenous insulin secretion in pancreatic beta cells. Sulfonylureas (e.g., tolbutamide and glipizide) or meglitinide are examples of drugs that stimulate insulin secretion (i.e., insulin secretagogues) thereby increasing circulating insulin concentrations high enough to stimulate insulin-resistant tissue. However, insulin and insulin secretagogues can lead to dangerously low glucose concentrations (i.e., hypoglycemia). In addition, insulin secretagogues frequently lose therapeutic potency over time.

Two biguanides, metformin and phenformin, can improve insulin sensitivity and glucose metabolism in diabetic patients. However, the mechanism of action is not well understood. Both compounds can lead to lactic acidosis and gastrointestinal side effects (e.g., nausea or diarrhea).

Alpha-glucosidase inhibitors (e.g., acarbose) can delay carbohydrate absorption from the gut after meals, which can in turn lower blood glucose levels, particularly in the postprandial period. Like biguanides, these compounds can also cause gastrointestinal side effects.

Glitazones (i.e., 5-benzylthiazolidine-2,4-diones) are a newer class of compounds used in the treatment of Type 2 diabetes. These agents can reduce insulin resistance in multiple tissues, thus lowering blood glucose. The risk of hypoglycemia can also be avoided. Glitazones modify the activity of the Peroxisome Proliferator Activated Receptor ("PPAR") gamma subtype. PPAR is currently believed to be the primary therapeutic target for the main mechanism of action for the beneficial effects of these compounds. Other modulators of the PPAR family of proteins are currently in development for the treatment of Type 2 diabetes and/or dyslipidemia. Marketed glitazones suffer from side effects including bodyweight gain and peripheral edema.

Additional treatments to normalize blood glucose levels in patients with diabetes mellitus are needed. Other therapeutic strategies are being explored. For example, research is being conducted concerning Glucagon-Like Peptide 1 ("GLP-1") analogues and inhibitors of Dipeptidyl Peptidase IV ("DPP-IV") that increase insulin secretion. Other examples include inhibitors of key enzymes involved in the hepatic glucose production and secretion (e.g., fructose-1,6-bisphosphatase inhibitors) and direct modulation of enzymes involved in insulin signaling (e.g., Protein Tyrosine Phosphatase-1B, or "PTP-1B").

Another method of treating or prophylactically treating diabetes mellitus includes using inhibitors of 11-β-hydroxysteroid dehydrogenase Type 1 (11β-HSD1). Such methods are discussed in J. R. Seckl et al., Endocrinology, 142: 1371-1376, 2001 and various references cited therein. 11β-HSD1, which is highly expressed in liver and adipose tissue, is an enzyme that converts cortisone to cortisol, which leads to higher local concentration of cortisol. Cortisol (in humans) is an active form of a glucocorticoid, while cortisone (in humans) is an inactive form of glucocorticoid. Glucocorticoids are steroid hormones that are potent regulators of glucose and lipid metabolism. Excessive glucocorticoid action can lead to insulin resistance, Type 2 diabetes, dyslipidemia, increased abdominal obesity, and hypertension. Therefore, inhibition of 11-HSD1 prevents or decreases the tissue specific amplification of glucocorticoid action and imparts beneficial effects on blood pressure and glucose- and lipid-metabolism.

Accordingly, there is a need for compounds that inhibit 11β-HSD1 to benefit patients suffering from non-insulin dependent type 2 diabetes, insulin resistance, obesity, lipid disorders, metabolic syndrome and other diseases and conditions mediated by excessive glucocorticoid action.

SUMMARY OF THE INVENTION

The present invention is directed towards a compound of formula (I):

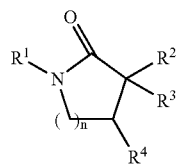

or a pharmaceutically acceptable salt, prodrug, salt of a prodrug, or a combination thereof, wherein:

n is 1 or 2;

$R^1$ is cycloalkyl or heterocycle, each of which is independently unsubstituted or substituted with 1, 2, 3 or 4 substituents independently selected from the group consisting of alkyl, alkenyl, haloalkyl, Cl, Br, F, I, —CN, —NO$_2$, —OR$_b$, —SR$_b$, —S(O)R$_Z$, —S(O)$_2$R$_Z$, —N$_a$R$_b$, —C(O)R$_b$, —C(O)OR$_b$, —C(O)NR$_a$R$_b$, —S(O)$_2$NR$_a$R$_b$, —C(=NOH)NH$_2$, —C(=NH)NH$_2$, R$_c$, —(CR$_d$R$_e$)$_m$—CN, —(CR$_d$R$_e$)$_m$—OR$_b$, —(CR$_d$R$_e$)$_m$—SR$_b$, —(CR$_d$R$_e$)$_m$—S(O)$_2$R$_Z$, —(CR$_d$R$_e$)$_m$—NR$_a$R$_b$, —(CR$_d$R$_e$)$_m$—C(O)R$_b$, —(CR$_d$R$_e$)$_m$—C(O)OR$_b$, —(CR$_d$R$_e$)$_m$—S(O)$_2$NR$_a$R$_b$, —(CR$_d$R$_e$)$_m$—R$_c$ —N(R$_a$)—(CR$_d$R$_e$)$_m$—C(O)R$_b$, —N(R$_a$)—(CR$_d$R$_e$)$_m$—C(O)OR$_b$, —N(R$_a$)—(CR$_d$R$_e$)$_m$—C(O)NR$_a$R$_b$, —O—(CR$_d$R$_e$)$_m$—C(O)R$_b$, —O—(CR$_d$R$_e$)$_m$—, —C(O)OR$_b$, and —O—(C$_d$R$_e$)$_m$—C(O)NR$_a$R$_b$;

$R^2$ and $R^3$ are each independently hydrogen, alkyl, R$_c$, or —(CR$_d$R$_e$)$_m$—R$_c$ or $R^2$ and $R^3$ taken together with the atoms to which they are attached form a cycloalkyl, $R^4$ is -E-G or —(CR$_d$R$_e$)$_m$-E-G, wherein E, at each occurrence, is independently O, S, S(O), S(O)$_2$, N(R$_e$) or a bond; G, at each occurrence, is independently alkyl, haloalkyl, —(CR$_d$D$_e$)$_m$—OR$_d$, —(CR$_d$R$_e$)$_m$—C(O)OR$_d$, —R$_A$, or —(CR$_d$R$_e$)$_m$—R$_A$, wherein R$_A$ at each occurrence is independently selected from the group consisting of aryl, heteroaryl, cycloalkyl and heterocycle, and each R$_A$ is independently unsubstituted or substituted with 1, 2, 3 or 4 substituents independently selected from the group consisting of alkyl, alkenyl, haloalkyl, Cl, Br, F, I, —CN, —NO$_2$, —OR$_d$, —S(R$_d$), —S(O)(alkyl), —S(O)(haloalkyl), —S(O)$_2$(alkyl), —S(O)$_2$(haloalkyl), —NR$_d$R$_e$, —C(O)(R$_d$), —C(O)OR$_d$, —C(O)NR$_d$R$_e$, —S(O)$_2$NR$_d$R$_e$, R$_c$, —(CR$_d$R$_e$)$_m$—CN, —(CR$_d$R$_e$)$_m$—NO$_2$, —(CR$_d$R$_e$)$_m$—OR$_d$, —(CR$_d$R$_e$)$_m$—S(R$_d$), —(CR$_d$R$_e$)$_m$—S(O)(alkyl), —(CR$_d$R$_e$)$_m$—S(O)(haloalkyl), —(CR$_d$R$_e$)$_m$—S(O)$_2$(alkyl), —(CR$_d$R$_e$)$_m$—S(O)$_2$(haloalkyl), —(CR$_d$R$_e$)$_m$—NR$_d$R$_e$, —(C$_d$R$_e$)$_m$—C(O)(R$_d$), —(CR$_d$R$_e$)$_m$—C(O)OR$_d$, —(CR$_d$R$_e$)$_m$—C(O)NR$_d$R$_e$, —(CR$_d$R$_e$)$_m$—S(O)$_2$NR$_d$R$_e$, and —(C$_d$R$_e$)$_m$—R$_c$;

R$_a$, at each occurrence, is independently hydrogen or alkyl;

R$_b$, at each occurrence, is independently hydrogen, alkyl, haloalkyl, R$_c$, or —(CR$_d$R$_e$)$_m$—R$_c$;

R$_Z$, at each occurrence, is independently alkyl, haloalkyl, R$_c$, or —(CR$_d$R$_e$)$_m$—R$_c$;

R$_c$, at each occurrence, is independently aryl, heteroaryl, cycloalkyl or heterocycle, wherein each R$_c$ is independently unsubstituted or substituted with 1, 2, 3 or 4 substituents independently selected from the group consisting of alkyl, alkenyl, haloalkyl, Cl, Br, F, I, —CN, —NO$_2$, —OR$_d$, —S(R$_d$), —S(O)(alkyl), —S(O)(haloalkyl), —S(O)$_2$(alkyl), —S(O)$_2$(haloalkyl), —NR$_d$R$_e$, —C(O)(R$_d$), —C(O)OR$_d$, —C(O)NR$_d$R$_e$, —S(O)$_2$NR$_d$R$_e$, —(CR$_d$R$_e$)$_m$—CN, —(CR$_d$R$_e$)$_m$—NO$_2$, —(CR$_d$R$_e$)$_m$—OR$_d$, —(CR$_d$R$_e$)$_m$—S(R$_d$), —(CR$_d$R$_e$)$_m$—S(O)(alkyl), —(CR$_d$R$_e$)$_m$—S(O)(haloalkyl), —(CR$_d$R$_e$)$_m$—S(O)$_2$(alkyl), —(CR$_d$R$_e$)$_m$—S(O)$_2$(haloalkyl), —(CR$_d$R$_e$)$_m$—NR$_d$R$_e$, —(CR$_d$R$_e$)$_m$—C(O)(R$_d$), —(CR$_d$R$_e$)$_m$—C(O)OR$_d$, —(CR$_d$R$_e$)$_m$—C(O)NR$_d$R$_e$, and —(CR$_d$R$_e$)$_m$—S(O)$_2$NR$_d$R$_e$;

R$_d$ and R$_e$, at each occurrence, are independently hydrogen, alkyl or haloalkyl; and m is 0, 1, 2, 3, 4, 5 or 6.

In addition, the present invention is directed towards methods of inhibiting the 11-beta-hydroxysteroid dehydrogenase Type 1 enzyme. Further, the present invention is directed towards methods of treating non-insulin dependent type 2 diabetes, insulin resistance, obesity, lipid disorders, metabolic syndrome and other diseases and conditions that are mediated by excessive glucocorticoid action by administering a therapeutically effective amount of a compound of formula (I). Finally, the present invention is directed towards a pharmaceutical composition including a therapeutically effective amount of a compound of formula (I) and a pharmaceutically acceptable carrier.

DETAILED DESCRIPTION OF THE INVENTION

Generally, the present invention is directed towards compounds that are inhibitors of the 11-beta-hydroxysteroid dehydrogenase Type 1 enzyme. The present invention is further directed towards methods of inhibiting 11-beta-hydroxysteroid dehydrogenase Type 1 enzyme for the treatment of non-insulin dependent type 2 diabetes, insulin resistance, obesity, lipid disorders, metabolic syndrome and other diseases and conditions that are mediated by excessive glucocorticoid action.

As set forth herein, for a variable that occurs more than one time in any substituent, in the compound of the invention, or any other formulae herein, its definition on each occurrence is independent of its definition at every other occurrence.

As used herein, the term "alkenyl" means, but is not limited to, a straight or branched chain hydrocarbon including from 2 to 10 carbons and including at least one carbon-carbon double bond formed by the removal of two hydrogens. Representative examples of an alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkyl" means, but is not limited to, straight or branched chain hydrocarbon including from 1 to 10 carbon atoms. Representative examples of an alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

As used herein, the term "$C_{1-6}$ alkyl" means, but is not limited to, a straight or branched chain hydrocarbon, including 1 to 6 carbon atoms. Examples include, but are not limited to, methyl, ethyl, n-propyl, iso-propyl, n-butyl, sec-butyl, iso-butyl, tert-butyl, n-pentyl, isopentyl, neopentyl, and n-hexyl.

As used herein, the term "aryl" means, but is not limited to, a phenyl group or a bicyclic hydrocarbon fused ring system including zero heteroatom and that one or more of the fused rings is a phenyl group. Bicyclic hydrocarbon fused ring systems are exemplified by a phenyl group fused to a monocyclic cycloalkyl group, as defined herein, a monocyclic cycloalkenyl group, as defined herein, or another phenyl group. The aryl groups of the present invention are appended to the parent moiety through any substitutable atom in the group. The aryl groups of the present invention can be unsubstituted or substituted. Representative examples of an aryl include, but are not limited to, 2,3-dihydro-1H-inden-1-yl, indan-4-yl, indan-5-yl, inden-1-yl, naphthyl, phenyl, 1,2,3,4-tetrahydronaphthalen-2-yl, and tetrahydronaphthalenyl.

As used herein, the term "cycloalkyl" or "cycloalkane" means, but is not limited to, a saturated monocyclic hydrocarbon ring system including three to eight carbon atoms and zero heteroatom. Examples of monocyclic ring systems include, but are not limited to, cyclopropyl, cyclobutyl, cyclopentyl, cyclohexyl, cycloheptyl, and cyclooctyl. The term "cycloalkyl" of the present invention also means a bicyclic fused ring system wherein the monocyclic cycloalkyl ring is fused to another monocyclic cycloalkyl group as defined herein. Examples of bicyclic cycloalkyls include, but are not limited to, bicyclo[5.1.0]octyl and bicycle[6.2.0]decanyl. The cycloalkyl groups of the present invention can be unsubstituted or substituted and are connected to the parent molecular moiety through any substitutable carbon atom of the group. The monocyclic and bicyclic cycloalkyls, as defined herein, can have one or two alkylene bridges of between one and three carbon atoms wherein each alkylene bridge connects two non-adjacent carbon atoms of the cycloalkyl ring systems. Representative examples of monocyclic or bicyclic ring systems that contain such connections between two non-adjacent carbon atoms include, but are not limited to, adamantyl, bicyclo[3.3.1]nonyl and bicyclo[2.2.2]octyl.

As used herein, the term "cycloalkenyl" or "cycloalkene" means, but is not limited to, a non-aromatic, partially unsaturated, monocyclic hydrocarbon ring system, having 4, 5, 6, 7 or 8 carbon atoms and zero heteroatom. The 4-membered ring systems have one double bond. The 5- or 6-membered ring systems have one or two double bonds, while the 7- or 8-membered ring systems have one, two or three double bonds. Representative examples of cycloalkenyl groups include, but are not limited to, cyclobutenyl, cyclopentenyl, cyclohexenyl, cycloheptenyl, and cyclooctenyl. The cycloalkenyl groups of the present invention can be unsubstituted or substituted and are attached to the parent molecular moiety through any substitutable carbon atom of the group.

As used herein, the term "halo" or "halogen" means —Cl, —Br, —I, or —F.

As used herein, the term "haloalkyl" means, but is not limited to, an alkyl group, as defined herein, in which one, two, three, four, five or six hydrogen atoms are replaced by halogen. Representative examples of a haloalkyl include, but are not limited to, chloromethyl, 2-fluoroethyl, trifluoromethyl, pentafluoroethyl, and 2-chloro-3-fluoropentyl.

As used herein, the term "heterocycle" or "heterocyclic" means, but is not limited to, a monocyclic or bicyclic, non-aromatic, saturated or partially unsaturated ring system. Monocyclic ring systems are exemplified by a 4-membered ring including one heteroatom independently selected from oxygen, nitrogen and sulfur; or a 5-, 6-, 7-, or 8-membered ring including one, two or three heteroatoms wherein the heteroatoms are independently selected from nitrogen, oxygen, and sulfur. The 5-membered ring has 0 or 1 double bond. The 6-memebered ring has 0, 1, or 2 double bonds. The 7- or 8-membered ring has 0, 1, 2, or 3 double bonds. Representative examples of monocyclic ring systems include, but are not limited to, azetidinyl, azepanyl, azepinyl, diazepinyl, dioxolanyl, dioxanyl, dithianyl, imidazolinyl, imidazolidinyl, isothiazolinyl, isothiazolidinyl, isoxazolinyl, isoxazolidinyl, morpholinyl, 3-oxo-morpholinyl, oxadiazolinyl, oxadiazolidinyl, oxazolinyl, 2-oxo-oxazolinyl, oxazolidinyl, piperazinyl, piperidyl, pyranyl, pyrazolinyl, pyrazolidinyl, pyrrolinyl, pyrrolidinyl, tetrahydrofuryl, tetrahydropyranyl, tetrahydropyridyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, 1,4-diazepanyl, and trithianyl. Bicyclic ring systems are exemplified by any of the above monocyclic ring systems fused to a phenyl group, a monocyclic cycloalkenyl group, as defined herein, a monocyclic cycloalkyl group, as defined herein, or an additional monocyclic heterocycle group, as defined herein. Representative examples of bicyclic ring systems include, but are not limited to, benzodioxinyl, benzodioxolyl, benzopyranyl, benzothiopyranyl, 2,3-dihydroindol-3-yl, 2,3-dihydrobenzofuran-3-yl, 2,3-dihydrobenzothien-3-yl, 2,3-dihydroisoindol-3-yl, 1,3-dihydro-isobenzofuran-3-yl, 1,3-dihydro-benzo[c]thien-3-yl, tetrahydroisoquinolinyl, tetrahydroquinolinyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, and octahydropyrrolo[3,4-c]pyrrolyl. The monocyclic or bicyclic ring systems as defined herein can have two of the non-adjacent carbon atoms connected by a heteroatom selected from nitrogen, oxygen, or sulfur, or an alkylene bridge of between one and three additional carbon atoms. Representative examples of monocyclic or bicyclic ring systems that contain such connection between two non-adjacent carbon atoms include, but are not limited to, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.1.1]heptyl, 6-oxa-3-azabicyclo[3.1.1]heptyl, 8-azabicyclo[3.2.1]octyl, 8-azabicyclo[3.2.1]oct-8-yl, 3-oxa-8-azabicyclo[3.2.1]octyl, 1,4-diazabicyclo[3.2.2]nonyl, 1,4-diazatricyclo[4.3.1.1$^{3,8}$]undecyl, 3,10-diazabicyclo[4,3,1]decyl, 8-oxa-3-azabicyclo[3.2.1]octyl, octahydro-1H-4,7-methanoisoindolyl, and octahydro-1H-4,7-epoxyisoindolyl. The heterocycle groups of the invention are substituted or unsubstituted, and are connected to the parent molecular moiety through any substitutable carbon or nitrogen atom in the groups. The nitrogen heteroatom can or cannot be quaternized, and the nitrogen or sulfur heteroatom can or cannot be oxidized. In addition, the nitrogen including heterocyclic rings can or cannot be N-protected.

As used herein, the term "heteroaryl" means, but is not limited to, an aromatic five- or six-membered ring where at least one atom is selected from the group consisting of N, O, and S, and the remaining atoms are carbon. The five membered rings have two double bonds, and the six membered rings have three double bonds. The term "heteroaryl" also includes bicyclic systems where a monocyclic heteroaryl ring is fused to a phenyl group, a monocyclic cycloalkyl group, as defined herein, a monocyclic cycloalkenyl group, as defined herein, a monocyclic heterocycle group, as defined herein, or an additional monocyclic heteroaryl group. Representative examples of heteroaryl groups include, but are not limited to, benzothienyl, benzoxazolyl, benzimidazolyl, benzoxadiazolyl, 6,7-dihydro-1,3-benzothiazolyl, furyl, imidazolyl, imidazo[1,2-a]pyridinyl, indazolyl, indolyl, isoindolyl, isoxazolyl, isoquinolinyl, isothiazolyl, naphthyridinyl, oxadiazolyl, oxazolyl, pyridoimidazolyl, pyridyl, pyridazinyl, pyrimidinyl, pyrazinyl, pyrazolyl, pyrrolyl, quinolinyl, thiazolyl, thienyl, triazolyl, thiadiazolyl, tetrazolyl, 1,2,3,4-tetrahydro-1,8-naphthyridin-2-yl, and 5,6,7,8-tetrahydroquinolin-5-yl. The heteroaryl groups of the present invention can be substituted or unsubstituted and are connected to the parent molecular moiety through any substitutable carbon or nitrogen atom in the groups. In addition, the nitrogen heteroatom can or cannot be quaternized. Further, the nitrogen and the sulfur atoms in the group can or cannot be oxidized. Also, the nitrogen including rings can or cannot be N-protected.

As used herein, the term "heteroatom" as used herein, refers to nitrogen, oxygen or sulfur atom.

As described herein, the present invention is directed towards a compound of formula (I):

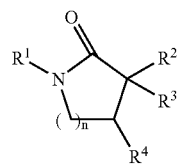

(I)

or a pharmaceutically acceptable salt, prodrug, salt of a prodrug, or a combination thereof, wherein:

n is 1 or 2;

$R^1$ is cycloalkyl or heterocycle, each of which is independently unsubstituted or substituted with 1, 2, 3 or 4 substituents independently selected from the group consisting of alkyl, alkenyl, haloalkyl, Cl, Br, F, I, —CN, —NO$_2$, —OR$_b$, —SR$_b$, —S(O)R$_Z$, —S(O)$_2$R$_Z$, —N$_a$R$_b$, —C(O)R$_b$, —C(O)OR$_b$, —C(O)NR$_a$R$_b$, —S(O)$_2$NR$_a$R$_b$, —C(=NOH)NH$_2$, —C(=NH)NH$_2$, R$_c$, —(CR$_d$R$_e$)$_m$—CN, —(CR$_d$R$_e$)$_m$—OR$_b$, —(CR$_d$R$_e$)$_m$—SR$_b$, —(CR$_d$R$_e$)$_m$—S(O)$_2$R$_Z$, —(CR$_d$R$_e$)$_m$—NR$_a$R$_b$, —(CR$_d$R$_e$)$_m$—C(O)R$_b$, —(CR$_d$R$_e$)$_m$—C(O)OR$_b$, —(CR$_d$R$_e$)$_m$—S(O)$_2$NR$_a$R$_b$, —(CR$_d$R$_e$)$_m$—R$_c$, —N(R$_a$)—(CR$_d$R$_e$)$_m$—C(O)R$_b$, —N(R$_a$)—(CR$_d$R$_e$)$_m$—C(O)OR$_b$, —N(R$_a$)—(CR$_d$R$_e$)$_m$—C(O)NR$_a$R$_b$, —O—(CR$_d$R$_e$)$_m$—C(O)R$_b$, —O—(C$_d$R$_e$)$_m$—C(O)OR$_b$, and —O—(CR$_d$R$_e$)$_m$—C(O)NR$_a$R$_b$;

$R^2$ and $R^3$, at each occurrence, are each independently hydrogen, alkyl, R$_e$, or —(C$_d$R$_e$)$_m$—R$_c$ or $R^2$ and $R^3$ taken together with the atoms to which they are attached form a cycloalkyl;

$R^4$ is -E-G or —(CR$_d$R$_e$)$_m$-E-G, wherein E, at each occurrence, is independently O, S, S(O), S(O)$_2$, N(R$_e$), or a bond and G, at each occurrence, is independently alkyl, haloalkyl, —(CR$_d$R$_e$)$_m$—OR$_d$, —(CR$_d$R$_e$)$_m$—C(O)OR$_d$, —R$_A$, or —(CR$_d$R$_e$)$_m$—R$_A$, wherein R$_A$, at each occurrence, is independently selected from the group consisting of aryl, heteroaryl, cycloalkyl and heterocycle, and each R$_A$ is independently unsubstituted or substituted with 1, 2, 3 or 4 substituents independently selected from the group consisting of alkyl, alkenyl, haloalkyl, Cl, Br, F, I, —CN, —NO$_2$, —OR$_d$, —S(R$_d$), —S(O)(alkyl), —S(O)(haloalkyl), —S(O)$_2$(alkyl), —S(O)$_2$(haloalkyl), —NR$_d$R$_e$, —C(O)(R$_d$), —C(O)OR$_d$, —C(O)NR$_d$R$_e$, —S(O)$_2$NR$_d$R$_e$, R$_c$, —(CR$_d$R$_e$)$_m$—CN, —(CR$_d$R$_e$)$_m$—NO$_2$, —(CR$_d$R$_e$)$_m$—OR$_d$, —(CR$_d$R$_e$)$_m$—S(R$_d$), —(CR$_d$R$_e$)$_m$—S(O)(alkyl), —(CR$_d$R$_e$)$_m$—S(O)(haloalkyl), —(CR$_d$R$_e$)$_m$—S(O)$_2$(alkyl), —(CR$_d$R$_e$)$_m$—S(O)$_2$(haloalkyl), —(CR$_d$R$_e$)$_m$—NR$_d$R$_e$, —(CR$_d$R$_e$)$_m$—C(O)(R$_d$), (CR$_d$R$_e$)$_m$—C(O)OR$_d$, —(CR$_d$R$_e$)$_m$—C(O)NR$_d$R$_e$, and —(CR$_d$R$_e$)$_m$—R$^c$;

$R_a$, at each occurrence, is independently hydrogen or alkyl;

$R_b$, at each occurrence, is independently hydrogen, alkyl, haloalkyl, R$_e$, or —(CR$_d$R$_e$)$_m$—R$_c$;

$R_Z$, at each occurrence, is independently alkyl, haloalkyl, R$_e$, or —(CR$_d$R$_e$)$_m$—R$_c$;

$R_c$, at each occurrence, is independently aryl, heteroaryl, cycloalkyl or heterocycle, wherein each R$_c$ is independently unsubstituted or substituted with 1, 2, 3, or 4 substituents independently selected from the group consisting of alkyl, alkenyl, haloalkyl, Cl, Br, F, I, —CN, —NO$_2$, —OR$_d$, —S(R$_d$), —S(O)(alkyl), —S(O)(haloalkyl), —S(O)$_2$(alkyl), —S(O)$_2$(haloalkyl), —NR$_d$R$_e$, —C(O)(R$_d$), —C(O)OR$_d$, —C(O)NR$_d$R$_e$, —S(O)$_2$NR$_d$R$_e$, —(CR$_d$R$_e$)$_m$—CN, —(CR$_d$R$_e$)$_m$—NO$_2$, —(CR$_d$R$_e$)$_m$—OR$_d$, —(CR$_d$R$_e$)$_m$—S(R$_d$), —(CR$_d$R$_e$)$_m$—S(O)(alkyl), —(CR$_d$R$_e$)$_m$—S(O)(haloalkyl), —(CR$_d$R$_e$)$_m$—S(O)$_2$(alkyl), —(CR$_d$R$_e$)$_m$—S(O)$_2$(haloalkyl), —(CR$_d$R$_e$)$_m$—NR$_d$R$_e$, —(CR$_d$R$_e$)$_m$—C(O)(R$_d$), —(CR$_d$R$_e$)$_m$—C(O)OR$_d$, —(CR$_d$R$_e$)$_m$—C(O)NR$_d$R$_e$, and —(CR$_d$R$_e$)$_m$—S(O)$_2$NR$_d$R$_e$;

R$_d$ and R$_e$, at each occurrence, are independently hydrogen, alkyl or haloalkyl; and m is 0, 1, 2, 3, 4, 5, or 6.

Compounds of formula (I) also include those where $R^1$ is a cycloalkyl or heterocycle, each of which is independently unsubstituted or substituted as described herein. More particularly, $R^1$ can be

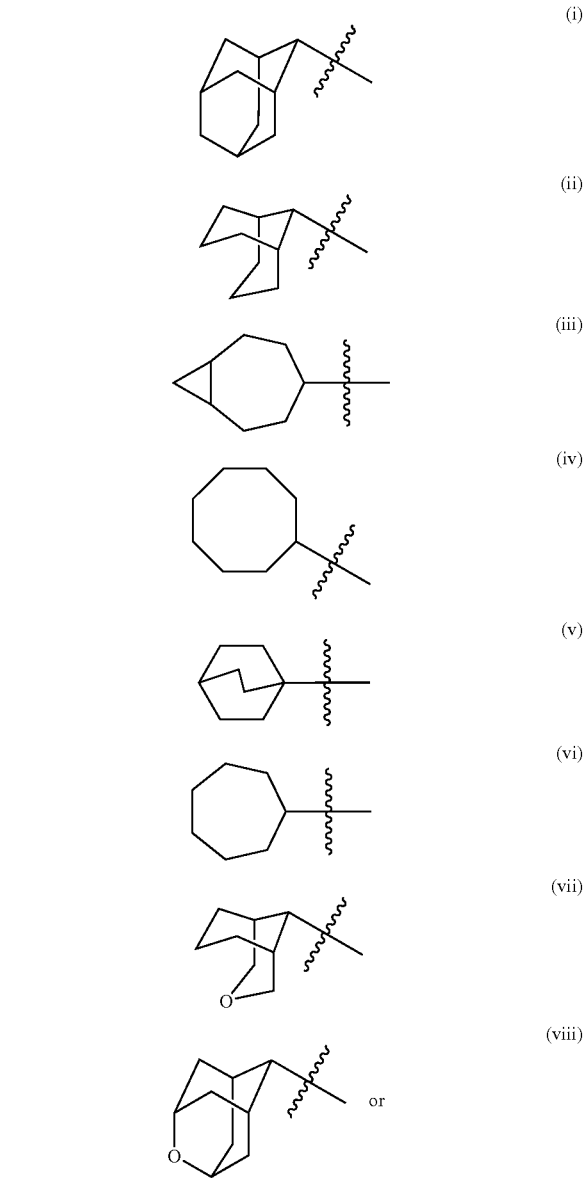

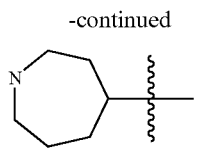

wherein each is independently unsubstituted or substituted as described herein. Further, n is 1 or 2 (preferably n is 1). Additionally, $R^2$ and $R^3$, at each occurrence, are each independently hydrogen, alkyl, $R_e$ or $-(CR_dR_e)_m-R_e$, wherein $R_e$, $R_d$, $R_e$ and m are as described herein (particularly, $R^2$ and $R^3$ are each independently $C_{1-6}$ alkyl and more particularly, $R^2$ and $R^3$ are methyl). $R^4$ is -E-G or $-(CR_dR_e)_m$-E-G, wherein E, G, $R_d$, $R_e$, and m are as described herein (particularly, $R^4$ is $-(CR_dR_e)_m-$O-G or $-(CR_dR_e)_m-N(R_e)$-G, wherein G, $R_d$, $R_e$, and m are as described herein, and more particularly, $R^4$ is $-(CH_2)-$O-G or $-(CH_2)-N(R_e)$-G wherein G and $R_e$ are as described herein). Preferably, $R^4$ is $-(CH_2)-$O-G or $-(CH_2)-N(R_e)$-G, wherein G, at each occurrence, is independently aryl or heteroaryl, each of which is independently unsubstituted or substituted as described herein, and $R_e$ is hydrogen, alkyl or haloalkyl. More preferably, $R^4$ is $-(CH_2)-$O-G or $-(CH_2)-N(R_e)$-G, wherein G, at each occurrence, is independently phenyl or pyridyl, wherein the phenyl and the pyridyl are each independently unsubstituted or substituted as described herein and $R_e$ is hydrogen or $C_{1-6}$ alkyl.

It is appreciated that the present invention contemplates compounds of formula (I) with combinations of the above embodiments, including preferred, more preferred and most preferred embodiments. Accordingly, one embodiment of the present invention is directed towards compounds of formula (I), or a pharmaceutically acceptable salt, prodrug, salt of a prodrug, or a combination thereof, wherein $R^4$ is $-(CR_dR_e)_m$-E-G, and $R_d$, $R_e$, m, E, G, $R^1$, $R^2$, $R^3$, and n are as described herein.

Another embodiment of the present invention is directed towards compounds of formula (I), or a pharmaceutically acceptable salt, prodrug, salt of a prodrug, or a combination thereof, wherein $R^4$ is $-(CR_dR_e)_m$-E-G and E is O or $-N(R_e)$, $R_d$ and $R_e$ are each independently hydrogen or $C_{1-6}$ alkyl, and m, G, $R^1$, $R^2$, $R^3$, and n are as described herein.

Another embodiment of the present invention is directed towards compounds of formula (I), or a pharmaceutically acceptable salt, prodrug, salt of a prodrug, or a combination thereof, wherein $R^4$ is $-(CR_dR_e)_m$-E-G, E is O or $-N(R_e)$, $R_d$ and $R_e$ are each independently hydrogen or $C_{1-6}$ alkyl, m is 1, n is 1, G is an aryl or heteroaryl, and $R^1$, $R^2$ and $R^3$ are as described herein.

Another embodiment of the present invention is directed towards compounds of formula (I), or a pharmaceutically acceptable salt, prodrug, salt of a prodrug, or a combination thereof, wherein $R^4$ is $-(CR_dR_e)_m$-E-G and E is O or $-N(R_e)$, $R_d$ and $R_e$ are each independently hydrogen or $C_{1-6}$ alkyl, m is 1, n is 1, G is an aryl or heteroaryl, $R^2$ and $R^3$ are each independently $C_{1-6}$ alkyl and $R^1$ is as described herein.

Another embodiment of the present invention is directed towards compounds of formula (I), or a pharmaceutically acceptable salt, prodrug, salt of a prodrug, or a combination thereof, wherein $R^1$ is cycloalkyl, unsubstituted or substituted and as described herein, $R^4$ is $-CH_2-$O-G or $-CH_2-N(R_e)$-G, wherein $R_e$ is hydrogen or $C_{1-6}$ alkyl, G is aryl or heteroaryl, each of which is unsubstituted or substituted as described herein, n is 1, and $R^2$ and $R_3$ are each independently $C_{1-6}$ alkyl.

Another embodiment of the present invention is directed towards compounds of formula (I), or a pharmaceutically acceptable salt, prodrug, salt of a prodrug, or a combination thereof, wherein $R^1$ is cycloalkyl, which is unsubstituted or substituted with one of the following substituents: $C_{1-6}$ alkyl, $-CN$, $-OR_b$, $-C(O)OR_b$, $-C(O)NR_aR_b$, $-C(=NOH)NH_2$, $-C(=NH)NH_2$, or heteroaryl, wherein $R_a$ and $R_b$ are each independently hydrogen or $C_{1-6}$ alkyl, $R^4$ is $-CH_2-$O-G or $CH_2-N(R_e)$-G, wherein $R_e$ is hydrogen or $C_{1-6}$ alkyl, G is aryl or heteroaryl, each of which is independently unsubstituted or substituted with one substituent such as haloalkyl, Cl, Br, F, I, $-CN$, or heteroaryl, n is 1, and $R^2$ and $R^3$ are each independently $C_{1-6}$ alkyl.

Another embodiment of the present invention is directed towards compounds of formula (I), or a pharmaceutically acceptable salt, prodrug, salt of a prodrug, or a combination thereof, wherein $R^1$ is

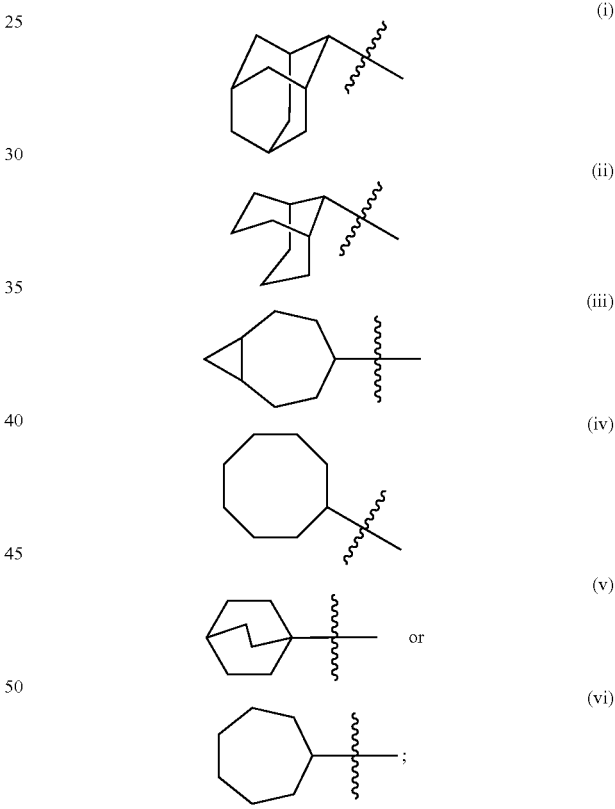

each of which is independently unsubstituted or substituted as described herein and $R^4$ is $-CH_2-$O-G or $-CH_2-N(R_e)$-G, wherein $R_e$ is hydrogen or methyl and G is phenyl or pyridyl, each of which is independently unsubstituted or substituted as described herein. Finally, $R^2$ and $R^3$, at each occurrence, are each methyl and n is 1.

A further embodiment of the present invention is directed towards compounds of formula (I), or a pharmaceutically acceptable salt, prodrug, salt of a prodrug, or a combination thereof, wherein $R^1$ is

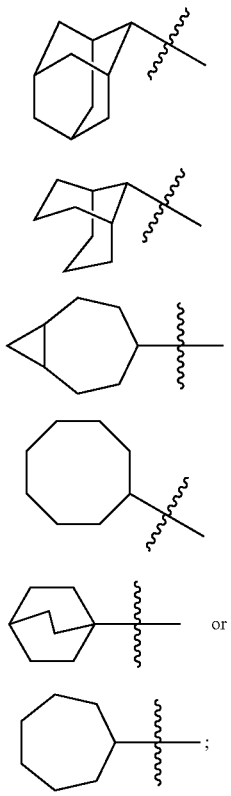

(i)

(ii)

(iii)

(iv)

(v)

or (vi)

;

each of which is independently unsubstituted or substituted with one substituent selected from methyl, —CN, —OH, or —C(O)OR$_b$, wherein R$_b$ is methyl or ethyl —C(O)NH$_2$, —C(=NOH)NH$_2$, —C(=NH)NH$_2$, and tetrazolyl, R$^4$ is —CH$_2$—O-G or —CH$_2$—N(R$_e$)-G, wherein R$_e$ is hydrogen or methyl, G is phenyl or pyridyl, each of which is independently unsubstituted or substituted with one substituent such as trifluoromethyl, Cl, Br, F, I, —CN, imidazolyl, triazolyl, or tetrazolyl, R$^2$ and R$^3$, at each occurrence, are methyl, and n is 1.

Another embodiment of the present invention is directed towards compounds of formula (I), or a pharmaceutically acceptable salt, prodrug, salt of a prodrug, or a combination thereof, wherein R$^1$ is a heterocycle, unsubstituted or substituted as described herein, R$^4$ is —CH$_2$—O-G or —CH$_2$—N(R$_e$)-G, wherein R$_e$ is hydrogen or C$_{1-6}$ alkyl, G is an aryl or heteroaryl, each of which is unsubstituted or substituted as described herein, n is 1, and R$^2$ and R$^3$ are C$_{1-6}$ alkyl.

An additional embodiment is directed towards compounds of formula (I), or a pharmaceutically acceptable salt, prodrug, salt of a prodrug, or a combination thereof, wherein R$^1$ is heterocycle, unsubstituted or substituted with one substituent selected from the group consisting of C$_{1-6}$ alkyl, —CN, —OR$_b$, —C(O)OR$_b$, —C(O)NR$_a$R$_b$, —C(=NOH)NH$_2$, —C(=NH)NH$_2$, and heteroaryl, wherein R$_a$ and R$_b$ are each independently hydrogen or C$_{1-6}$ alkyl, R$^4$ is —CH$_2$—O-G or —CH$_2$—N(R$_e$)-G, wherein R$_e$ is hydrogen or C$_{1-6}$ alkyl, G is an aryl or heteroaryl, each of which is independently unsubstituted or substituted with one substituent such as a haloalkyl, Cl, Br, F. I, —CN, or heteroaryl, n is 1, and R$^2$ and R$^3$, at each occurrence, are each C$_{1-6}$ alkyl.

Another embodiment of the present invention is directed towards compounds of formula (I), or a pharmaceutically acceptable salt, prodrug, salt of a prodrug, or a combination thereof, wherein R$^1$ is

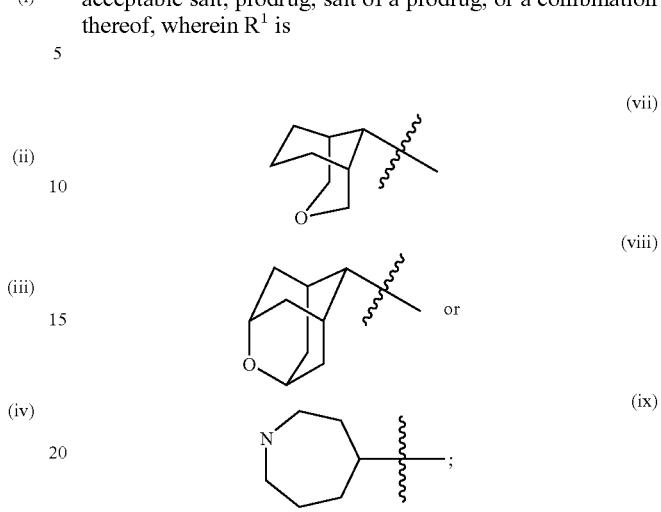

(vii)

(viii) or (ix) ;

each of which is independently unsubstituted or substituted as described herein, R$^4$ is —CH$_2$—O-G or —CH$_2$—N(R$_e$)-G, wherein R$_e$ is hydrogen or methyl, G is phenyl or pyridyl, each of which is independently unsubstituted or substituted as described herein, R$^2$ and R$^3$, are each methyl, and n is 1.

A further embodiment of the present invention is directed towards compounds of formula (I), or a pharmaceutically acceptable salt, prodrug, salt of a prodrug, or a combination thereof, wherein R$^1$ is

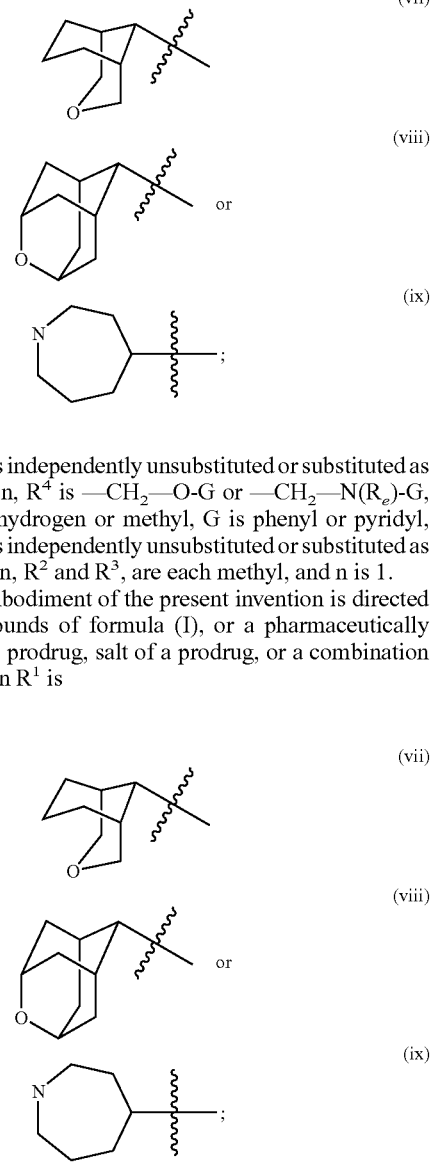

(vii)

(viii) or (ix) ;

each of which is independently unsubstituted or substituted with one substituent such as methyl, —CN, —OH, —C(O)OR$_b$ (wherein R$_b$ is methyl or ethyl), —C(O)NH$_2$, —C(=NOH)NH$_2$, —C(=NH)NH$_2$, or tetrazolyl, R$^4$ is —CH$_2$—O-G or —CH$_2$—N(R$_e$)-G, wherein R$_e$ is hydrogen or methyl, G is phenyl or pyridyl, each of which is independently unsubstituted or substituted with one substituent such as trifluoromethyl, Cl, Br, F, I, —CN, imidazolyl, triazolyl, and tetrazolyl, R$^2$ and R$^3$ are each methyl, and n is 1.

Exemplary compounds of the present invention include, but are not limited to,

6-[(1-cycloheptyl-4,4-dimethyl-5-oxopyrrolidin-3-yl)methoxy]nicotinonitrile;

4-(4-{[(5-cyanopyridin-2-yl)oxy]methyl}-3,3-dimethyl-2-oxopyrrolidin-1-yl)azepane-1-carboxamide;

1-cycloheptyl-3,3-dimethyl-4-(phenoxymethyl)pyrrolidin-2-one;

1-cycloheptyl-4-{[(2-fluorophenyl)(methyl)amino]methyl}-3,3-dimethylpyrrolidin-2-one;

6-{[1-(5-hydroxycyclooctyl)-4,4-dimethyl-5-oxopyrrolidin-3-yl]methoxy}nicotinonitrile;

E-4-(4-{[(5-cyanopyridin-2-yl)oxy]methyl}-3,3-dimethyl-2-oxopyrrolidin-1-yl)adamantane-1-carboxamide;

9-(4-{[(5-cyanopyridin-2-yl)oxy]methyl}-3,3-dimethyl-2-oxopyrrolidin-1-yl)bicyclo[3.3.1]nonane-3-carboxamide;

Trans ethyl (1R,7S)-4-(4-{[(5-cyanopyridin-2-yl)oxy]methyl}-3,3-dimethyl-2-oxopyrrolidin-1-yl)bicyclo[5.1.0]octane-8-carboxylate and trans ethyl (1S,7R)-4-(4-{[(5-cyanopyridin-2-yl)oxy]methyl}-3,3-dimethyl-2-oxopyrrolidin-1-yl)bicyclo[5.1.0]octane-8-carboxylate;

6-{[4,4-dimethyl-1-(4-methylbicyclo[2.2.2]oct-1-yl)-5-oxopyrrolidin-3-yl]methoxy}nicotinonitrile;

6-{[1-(5-cyanocyclooctyl)-4,4-dimethyl-5-oxopyrrolidin-3-yl]methoxy}nicotinonitrile;

E-4-(4-{[(5-cyanopyridin-2-yl)oxy]methyl}-3,3-dimethyl-2-oxopyrrolidin-1-yl)adamantane-1-carbonitrile;

E-4-(3,3-dimethyl-2-oxo-4-{[4-(1H-1,2,4-triazol-1-yl)phenoxy]methyl}pyrrolidin-1-yl)adamantane-1-carboxamide;

E-4-(4-{[4-(1H-imidazol-1-yl)phenoxy]methyl}-3,3-dimethyl-2-oxopyrrolidin-1-yl)adamantane-1-carboxamide;

E-4-[3,3-dimethyl-2-oxo-4-(([5-(trifluoromethyl)pyridin-2-yl]oxy}methyl)pyrrolidin-1-yl]-N'-hydroxyadamantane-1-carboximidamide;

E-4-[3,3-dimethyl-2-oxo-4-(([5-(trifluoromethyl)pyridin-2-yl]oxy}methyl)pyrrolidin-1-yl]adamantane-1-carboxamide; and E-4-[3,3-dimethyl-2-oxo-4-(([5-(trifluoromethyl)pyridin-2-yl]oxy}methyl)pyrrolidin-1-yl]adamantane-1-carboximidamide;

or a pharmaceutically acceptable salt, prodrug, salt of a prodrug, or a combination thereof.

The compounds of the present invention can exist as therapeutically acceptable salts. The term "therapeutically acceptable salt," refers to salts or zwitterions of the compounds that are water or oil-soluble or dispersible, suitable for treatment of disorders without undue toxicity, irritation and allergic response, commensurate with a reasonable benefit/risk ratio and effective for their intended use. The salts can be prepared during the final isolation and purification of the compounds or separately by reacting an amino group of the compounds with a suitable acid. For example, a compound can be dissolved in a suitable solvent, such as, but not limited to, methanol and water, and treated with at least one equivalent of an acid such as hydrochloric acid. The resulting salt can precipitate out and be isolated by filtration and dried under reduced pressure. Alternatively, the solvent and excess acid can be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, form ate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine and the like, are contemplated as being within the scope of the present invention.

The present compounds can also exist as pharmaceutically acceptable prodrugs. The term "pharmaceutically acceptable prodrug," refers to those prodrugs or zwitterions, which are suitable for use in contact with the tissues of patients without undue toxicity, irritation, and allergic response, are commensurate with a reasonable benefit/risk ratio, and are effective for their intended use. The term "prodrug," refers to compounds that are rapidly transformed in vivo to the parent compounds of formula (I), for example, by hydrolysis in blood. The term "prodrug," refers to compounds that contain, but are not limited to, substituents known as "therapeutically acceptable esters." The term "therapeutically acceptable ester" refers to alkoxycarbonyl groups appended to the parent molecule on an available carbon atom. More specifically, a "therapeutically acceptable ester" refers to alkoxycarbonyl groups appended to the parent molecule on one or more available aryl, cycloalkyl, and/or heterocycle groups as defined herein. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated herein by reference in their entirety.

Compounds including geometric isomers of carbon-carbon double bonds and carbon-nitrogen double are included in the present invention. Substituents around a carbon-carbon or a carbon-nitrogen double bond are designated as being of Z or E configuration and substituents around a cycloalkyl or heterocycloalkyl are designated as being of cis or trans configuration. Furthermore, substituents around an adamantane ring system are designated as being of Z or E relative configuration. For examples, see C. D. Jones, M. Kaselj, R. N. Salvatore, W. J. le Noble J. Org. Chem. 63: 2758-2760, 1998. All geometric isomeric forms and mixtures thereof of the compounds described herein are encompassed within the scope of the present invention.

Asymmetric centers exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well known in the art.

Compounds of this invention include at least one chiral center and can exist as single stereoisomers (e.g. single enantiomer), mixtures of stereoisomers (e.g. any mixture of enantiomers or diastereomers) or racemic mixtures thereof. As a result, all stereoisomers of the compounds of the invention are included in the present invention, including racemic mixtures, mixtures of diastereomers, mixtures of enantiomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral centers present in the chemical structures illustrated herein is not specified, the chemical structure is intended to encompass compounds including either stereoisomer of each chiral center present in the compound.

A further embodiment of the present invention is directed towards a pharmaceutical composition including a therapeutically effective amount of the compound of formula (I) of claim 1; and a pharmaceutically acceptable carrier.

Therapeutic compositions of the present compounds include an effective amount of the same formulated with one or more pharmaceutically acceptable carriers. The term "pharmaceutically acceptable carrier" as used herein, represents a non-toxic, solid, semi-solid or liquid filler, diluent, encapsulating material, or formulation auxiliary of any type. Examples of pharmaceutically acceptable carriers include, but are not limited to, sugars, cellulose and derivatives thereof, oils, glycols, solutions, buffering, coloring, releasing, coating, sweetening, flavoring, perfuming agents, and other pharmaceutically acceptable carriers known to those of skill in the art. These therapeutic compositions can be administered parenterally, intracisternally, orally, rectally, or intraperitoneally.

Liquid dosage forms for oral administration of the present compounds include formulations of the same as emulsions, microemulsions, solutions, suspensions, syrups, and elixirs. In addition to the compounds, the liquid dosage forms can include diluents and/or solubilizing or emulsifying agents. Besides inert diluents, the oral compositions can include wetting, emulsifying, sweetening, flavoring, and perfuming agents.

Injectable preparations of the present compounds include sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media.

Inhibition of 11-beta-hydroxysteroid dehydrogenase Type 1 enzyme by the compounds of the present invention can be delayed by using a liquid suspension of crystalline or amorphous material with poor water solubility. The rate of absorption of the compounds depends upon their rate of dissolution, which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage forms for oral administration of the present compounds include, but are not limited to, capsules, tablets, pills, powders, and granules. In such forms, the compound is mixed with at least one inert, therapeutically suitable excipient such as a carrier, filler, extender, disintegrating agent, solution-retarding agent, wetting agent, absorbent, or lubricant. With capsules, tablets, and pills, the excipient can also contain buffering agents. Suppositories for rectal administration can be prepared by mixing the compounds with a suitable non-irritating excipient that is solid at ordinary temperature but fluid in the rectum.

The compounds of the present invention can be microencapsulated with one or more of the excipients or carriers previously set forth above. The solid dosage forms of tablets, dragees, capsules, pills, and granules can be prepared with coatings and shells such as enteric and release-controlling. In these forms, the compounds of the present invention can be mixed with at least one inert diluent and can optionally include tableting lubricants and aids. Capsules can also optionally include opacifying agents that delay release of the compounds in a desired part of the intestinal tract.

Transdermal patches have the added advantage of providing controlled delivery of the compounds of the present invention to a body. Dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders that can be treated or prevented in a patient by administering to the patient, a therapeutically effective amount of the compound of the present invention in such an amount and for such time as is necessary to achieve the desired result. The term "therapeutically effective amount" refers to a sufficient amount of a compound of formula (I) to effectively ameliorate disorders by inhibiting 11-beta-hydroxysteroid dehydrogenase Type 1 enzyme at a reasonable benefit/risk ratio applicable to any medical treatment. The specific therapeutically effective dose level for any particular patient can depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of 11-beta-hydroxysteroid dehydrogenase Type 1 enzyme in single or divided doses can be in amounts, for example, from about 0.01 to 50 mg/kg body weight. In a more preferred range, compounds of the present invention inhibit the action of 11-beta-hydroxysteroid dehydrogenase Type 1 enzyme in a single or divided doses from about 0.05 to 25 mg/kg body weight. Single dose compositions can contain such amounts or submultiple doses thereof of the compounds of the present invention to make up the daily dose. In general, treatment regimens include administration to a patient in need of such treatment from about 1 mg to about 1000 mg of the compounds per day in single or multiple doses.

In addition to the above embodiments of the present invention that are directed towards various compounds, other embodiments of the present invention are directed towards various methods. In another embodiment of the present invention, there is provided a method of inhibiting 11-beta-hydroxysteroid dehydrogenase Type I enzyme by administering to a mammal, a therapeutically effective amount of the compound of formula (I), or a pharmaceutically acceptable salt, prodrug, salt of a prodrug, or a combination thereof.

A further embodiment of the present invention is directed towards a method of treating disorders in a mammal through the inhibition 11-beta-hydroxysteroid dehydrogenase Type I enzyme by administering to a mammal, a therapeutically effective amount of the compound of formula (I). Particularly, the disorders can be, but are not limited to, non-insulin dependent Type 2 diabetes, insulin resistance, obesity, lipid disorder, metabolic syndrome, or other diseases and conditions that are mediated by excessive glucocorticoid action. Yet another embodiment of the present invention is directed towards a method of treating diseases and conditions that are mediated through excessive glucocorticoid action in a mammal by inhibiting 11-beta-hydroxysteroid dehydrogenase Type I enzyme.

The various methods associated with the administration of the compound of formula (I) are based on the following principles. Glucocorticoids are steroid hormones that play an important role in regulating multiple physiological processes in a wide range of tissues and organs. For example, glucocorticoids are potent regulators of glucose and lipid metabolism. Excess glucocorticoid action can lead to insulin resistance, type 2 diabetes, dyslipidemia, visceral obesity and hypertension. Cortisol is the major active form and cortisone is the major inactive form of glucocorticoids in humans, while corticosterone and dehydrocorticosterone are the major active and inactive forms respectively in rodents.

Previously, the main determinants of glucocorticoid action were thought to be the circulating hormone concentration and the density of glucocorticoid receptors in the target tissues. In the last decade, it was discovered that tissue glucocorticoid levels can also be controlled by 11β-hydroxysteroid dehydrogenases enzymes (11β-HSDs). There are two 11β-HSD isozymes that have different substrate affinities and cofactors. The 11β-hydroxysteroid dehydrogenases type 1 enzyme (11β-HSD-1) is a low affinity enzyme with $K_m$ for cortisone in the micromolar range that prefers NADPH/NADP$^+$ (nicotinamide adenine dinucleotide) as cofactors. 11β-HSD-1 is widely expressed and particularly high expression levels are found in liver, brain, lung, adipose tissue and vascular smooth muscle cells. In vitro studies indicate that 11β-HSD-1 is capable of acting both as a reductase and a dehydrogenase. However, many studies have shown that it is predominantly a reductase in vivo and in intact cells. It converts inactive 11-ketoglucocorticoids (i.e., cortisone or dehydrocorticosterone) to active 11-hydroxyglucocorticoids (i.e., cortisol or corticosterone) and therefore amplifies the glucocorticoid action in a tissue-specific manner.

With only 20% homology to 11β-HSD-1, the 11β-hydroxysteroid dehydrogenases type 2 enzyme (11β-HSD-2) is a NAD$^+$-dependent, high affinity dehydrogenase with a $K_m$ for cortisol in the nanomolar range. 11β-HSD-2 is found primarily in mineralocorticoid target tissues, such as the kidney, colon, and placenta. Glucocorticoid action is mediated by the binding of glucocorticoids to receptors, such as mineralocorticoid receptors and glucocorticoid receptors. Through binding to its receptor, the main mineralocorticoid aldosterone controls the water and salts balance in the body. However, the mineralocorticoid receptors have a high affinity for both cortisol and aldosterone. 11β-HSD-2 converts cortisol to inactive cortisone, therefore preventing the non-selective mineralocorticoid receptors from being exposed to high levels of cortisol. Mutations in the gene encoding 11β-HSD-2 cause Apparent Mineralocorticoid Excess Syndrome (AME), which is a congenital syndrome resulting in hypokaleamia and severe hypertension. AME Patients have elevated cortisol levels in mineralocorticoid target tissues due to reduced 11β-HSD-2 activity. The AME symptoms can also be induced by administration of 11β-HSD-2 inhibitor, glycyrrhetinic acid. The activity of 11β-HSD-2 in placenta is probably important for protecting the fetus from excess exposure to maternal glucocorticoids, which can result in hypertension, glucose intolerance and growth retardation. Due to the potential side effects resulting from 11β-HSD-2 inhibition, the present invention describes selective 11β-HSD-1 inhibitors.

Glucocorticoid levels and/or activity can contribute to numerous disorders, including Type TI diabetes, obesity, dyslipidemia, insulin resistance, and hypertension. Administration of the compounds of the present invention decreases the level of cortisol and other 11β-hydroxysteroids in target tissues, thereby reducing the effects of glucucorticoid activity in key target tissues. The present invention could be used for the treatment, control, amelioration, prevention, delaying the onset of or reducing the risk of developing the diseases and conditions that are described herein.

Since glucocorticoids are potent regulators of glucose and lipid metabolism, glucocorticoid action can contribute or lead to insulin resistance, Type 2 diabetes, dyslipidemia, visceral obesity, and hypertension. For example, cortisol antagonizes the insulin effect in liver resulting in reduced insulin sensitivity and increased gluconeogenesis. Patients who already have impaired glucose tolerance have a greater probability of developing Type 2 diabetes in the presence of abnormally high levels of cortisol. Previous studies (B. R. Walker et al., J. of Clin. Endocrinology and Met., 80: 3155-3159, 1995) have demonstrated that administration of non-selective 11β-HSD-1 inhibitor, carbenoxolone, improves insulin sensitivity in humans. Therefore, administration of a therapeutically effective amount of an 11β-HSD-1 inhibitor can treat, control, ameliorate, delay, or prevent the onset of Type 2 diabetes.

Administration of glucocorticoids in vivo has been shown to reduce insulin secretion in rats (B. Billaudel et al., Horm. Metab. Res. 11: 555-560, 1979). It has also been reported that conversion of dehydrocorticosterone to corticosterone by 11β-HSD-1 inhibits insulin secretion from isolated murine pancreatic β cells (B. Davani et al., J. Biol. Chem., 275: 34841-34844, 2000). Further, and that incubation of isolated islets with an 11β-HSD-1 inhibitor improves glucose-stimulated insulin secretion (H Orstater et al., Diabetes Metab. Res. Rev. 21: 359-366, 2005). Therefore, administration of a therapeutically effective amount of an 11β-HSD-1 inhibitor can treat, control, ameliorate, delay, or prevent the onset of Type 2 diabetes by improving glucose-stimulated insulin secretion in the pancreas.

Abdominal obesity is closely associated with glucose intolerance (C. T. Montaque et al., Diabetes, 49: 883-888, 2000), hyperinsulinemia, hypertriglyceridemia, and other factors of metabolic syndrome (also known as syndrome X) such as high blood pressure, elevated VLDL, and reduced HDL. Animal data supporting the role of 11β-HSD-1 in the pathogenesis of the metabolic syndrome is extensive (Masuzaki, et al. *Science*. 294: 2166-2170, 2001; Paterson, J. M., et al.; *Proc Natl. Acad. Sci. USA*. 101: 7088-93, 2004; Montague and O'Rahilly. *Diabetes*. 49: 883-888, 2000). Therefore, administration of a therapeutically effective amount of an 11β-HSD-1 inhibitor can treat, control, ameliorate, delay, or prevent the onset of obesity. Long-term treatment with an 11β-HSD-1 inhibitor can also be useful in delaying the onset of obesity, or perhaps preventing it entirely if the patients use an 11β-HSD-1 inhibitor in combination with controlled diet, exercise, or in combination or sequence with other pharmacological approaches.

By reducing insulin resistance and/or maintaining serum glucose at normal concentrations and/or reducing obesity, compounds of the present invention also have utility in the treatment and prevention of conditions that accompany Type 2 diabetes and insulin resistance such as, but not limited to, metabolic syndrome or syndrome X, obesity, reactive hypoglycemia, diabetic dyslipidemia, and other conditions that accompany Type 2 diabetes and insulin resistance known to those of skill in the art.

In addition, 11β-HSD-1 is present in multiple tissues such as vascular smooth muscle, where local glucocorticoid levels that are thought to increase insulin resistance, lead to reductions in nitric oxide production, and potentiate the vasoconstrictive effects of both catecholamines and angiotensin II (M. Pirpiris et al., Hypertension, 19:567-574, 1992, C. Kornel et al., Steroids, 58: 580-587, 1993, B. R. Walker and B. C. Williams, Clin. Sci. 82:597-605, 1992; Hodge, G. et al Exp. Physiol 87: 1-8, 2002). High levels of cortisol in tissues where the mineralocorticoid receptor is present can lead to hypertension, as observed in Cushing's patients (See, D. N. Orth, N. Engl. J. Med. 332:791-803, 1995, M. Boscaro, et al., Lancet, 357: 783-791, 2001, X. Bertagna, et al, Cushing's Disease. In: Melmed S., Ed. The Pituitary. $2^{nd}$ ed. Malden, M A: Blackwell; 592-612, 2002). Transgenic mice overexpressing 11β-HSD-1 in liver and fat are also hypertensive, a phenotype believed to result from glucocorticoid activation of the renin angiotensin system (Paterson, J. M. et al, PNAS. 101: 7088-93, 2004; Masuzaki, H. et al, J. Clin. Invest. 112: 83-90, 2003). Therefore, administration of a therapeutically effective dose of an 11β-HSD-1 inhibitor can treat, control, ameliorate, delay, or prevent the onset of hypertension.

Another syndrome, Cushing's syndrome, is a life-threatening metabolic disorder characterized by sustained and elevated glucocorticoid levels caused by the endogenous and excessive production of cortisol from the adrenal glands. Typical Cushingoid characteristics include central obesity, diabetes and/or insulin resistance, moon face, buffalo hump, skin thinning, dyslipidemia, osteoporosis, reduced cognitive capacity, dementia, hypertension, sleep deprivation, and atherosclerosis among others (Principles and Practice of Endocrinology and Metabolism. Edited by Kenneth Becker, Lippincott Williams and Wilkins Publishers, Philadelphia, 2001; pg 723-8). The same characteristics can also arise from the exogenous administration of high doses of exogenous glucocorticoids, such as prednisone or dexamethasone, as part of an anti-inflammatory treatment regimen. Endogenous Cushings typically evolves from pituitary hyperplasia, some other ectopic source of ACTH, or from an adrenal carcinoma or nodular hyperplasia. Administration of a therapeutically effective dose of an 11-HSD-1 inhibitor can reduce local glucocorticoid concentrations and therefore treat, control, ameliorate, delay, or prevent the onset of Cushing's disease and/or similar symptoms arising from glucocorticoid treatment.

In Cushing's patients, excess cortisol levels contributes to the development of hypertension, dyslipidemia, insulin resistance, and obesity, conditions characteristic of metabolic syndrome (Orth, D. N. et al N. Engl. J. Med. 332:791-803, 1995; Boscaro, M. et al., Lancet, 357: 783-791, 2001, Bertagna, X. et al, Cushing's Disease. In: Melmed S., Ed. The Pituitary. $2^{nd}$ ed. Malden, M A: Blackwell; 592-612, 2002). Hypertension and dyslipidemia are also associated with development of atherosclerosis. 11β-HSD-1 knockout mice are resistant to the dyslipidemic effects of a high fat diet and have an improved lipid profile vs wild type controls (Morton N. M. et al, JBC, 276: 41293-41300, 2001), and mice which overexpress 11β-HSD-1 in fat exhibit the dyslipidemic phenotype characteristic of metabolic syndrome, including elevated circulating free fatty acids, and triclylgerides (Masuzaki, H., et al Science. 294: 2166-2170, 2001). Administration of a selective 11β-HSD-1 inhibitor has also been shown to reduce elevated plasma triglycerides and free fatty acids in mice on a high fat diet, and significantly reduce aortic content of cholesterol esters, and reduce progression of atherosclerotic plaques in mice (Hermanowski-Vosatka, A. et al. J. Exp. Med. 202: 517-27, 2005). The administration of a therapeutically effective amount of an 11β-HSD-1 inhibitor would therefore be expected to treat, control, ameliorate, delay, or prevent the onset of dyslipidemia and/or atherosclerosis.

Further, it is well known that 11-HSD-1 is expressed in mammalian brain, and published data indicates that glucocorticoids can cause neuronal degeneration and dysfunction, particularly in the aged (de Quervain et al.; *Hum Mol. Genet.* 13: 47-52, 2004; Belanoff et al. *J. Psychiatr Res.* 35: 127-35, 2001). Evidence in rodents and humans provide that prolonged elevation of plasma glucocorticoid levels impairs cognitive function that becomes more profound with aging. (Issa, A. M. et al. J. Neurosci. 10: 3247-54, 1990; Lupien, S. J et al. Nat. Neurosci. 1: 69-73, 1998; Yau, J. L. W. et al *Proc Natl Acad Sci USA.* 98: 4716-4712, 2001). Thekkapat et al has recently shown that 11β-HSD-1 mRNA is expressed in human hippocampus, frontal cortex and cerebellum, and that treatment of elderly diabetic individuals with the non-selective HSD½ inhibitor carbenoxolone improved verbal fluency and memory (*Proc Natl Acad Sci USA.* 101: 6743-9, 2004). Additional CNS effects of glucocorticoids include glucocorticoid-induced acute psychosis, which is of major concern to physicians when treating patients with these steroidal agents (Wolkowitz et al.; *Ann NY Acad. Sci.* 1032: 191-4, 2004). Conditional mutagenesis studies of the glucocorticoid receptor in mice have also provided genetic evidence that reduced glucocorticoid signaling in the brain results in decreased anxiety (Tronche, F. et al. (1999) Nature Genetics 23: 99-103). Therefore, it is expected that potent, selective 11β-HSD-1 inhibitors would treat, control, ameliorate, delay, or prevent the onset of cognitive decline, dementia, steroid-induced acute psychosis, depression, and/or anxiety.

Glucocorticoids are also known to cause a variety of skin related side effects including skin thinning, and impairment of wound healing (Anstead, G. *Adv Wound Care.* 11: 277-85, 1998; Beer, et al.; *Vitam Horm.* 59: 217-39, 2000). 11β-HSD-1 is expressed in human skin fibroblasts, and it has been shown that the topical treatment with the non-selective HSD½ inhibitor glycerrhetinic acid increases the potency of topically applied hydrocortisone in a skin vasoconstrictor assay (Hammami, M M, and Siiteri, P K. *J. Clin. Endocrinol. Metab.* 73: 326-34, 1991). Advantageous effects of selective 11β-HSD-1 inhibitors such as BVT.2733 on wound healing have also been reported (WO 2004/11310). High levels of glucocorticoids inhibit blood flow and formation of new blood vessels to healing tissues. In vitro and in vivo models of angiogenesis have shown that systemic antagonism with the glucocorticoid receptor RU-486 enhances angiogenesis in subcutaneous sponges as well as in mouse myocardium following coronary artery ligation (Walker, et al, PNAS, 102: 12165-70, 2005). 11β-HSD-1 knockout mice also showed enhanced angiogenesis in vitro and in vivo within sponges, wounds, and infarcted myocardium. It is therefore expected that potent, selective 11β-HSD-1 inhibitors would treat, control, ameliorate, delay, or prevent the onset of skin thinning and/or promote wound healing and/or angiogenesis.

Although cortisol is an important and well-recognized anti-inflammatory agent (J. Baxer, Pharmac. Ther., 2:605-659, 1976), if present in large amount it also has detrimental effects. In certain disease states, such as tuberculosis, psoriasis and stress in general, high glucocorticoid activity shifts the immune response to a humoral response, when in fact a cell based response can be more beneficial to patients. Inhibition of 11β-HSD-1 activity can reduce glucocorticoid levels, thereby shifting the immune response to a cell based response. (D. Mason, Immunology Today, 12: 57-60, 1991, G. A. W. Rook, Baillier's Clin. Endocrinol. Metab. 13: 576-581, 1999). Therefore, administration of 11β-HSD-1 specific inhibitors could treat, control, ameliorate, delay, or prevent the onset of tuberculosis, psoriasis, stress, and diseases or conditions where high glucocorticoid activity shifts the immune response to a humoral response.

One of the more significant side effects associated with topical and systemic glucocorticoid therapy is glaucoma, which results in serious increases in intraocular pressure, with the potential to result in blindness (Armaly et al.; *Arch Opthalmol.* 78: 193-7, 1967; Stokes et al.; *Invest Opthalmol V is Sci.* 44: 5163-7, 2003;). The cells that produce the majority of aqueous humor in the eye are the nonpigmented epithelial cells (NPE). These cells have been demonstrated to express 11β-HSD-1. Additionally, consistent with the expression of 11β-HSD-1, elevated ratios of cortisol:cortisone in the aqueous humor exist (Rauz et al. *Invest Opthalmol V is Sci.* 42: 2037-2042, 2001). Furthermore, it has been shown that patients who have glaucoma, but who are not taking exogenous steroids, have elevated levels of cortisol vs. cortisone in their aqueous humor (Rauz et al. *QJM.* 96: 481-490, 2003.) Treatment of patients with the nonselective HSD½ inhibitor carbenoxolone for 4 or 7 days significantly lowered intraocular pressure and local cortisol generation within the eye (Rauz et al.; *QJM.* 96: 481-490, 2003.). It is therefore expected that potent, selective 11β-HSD-1 inhibitors would treat, control, ameliorate, delay, or prevent the onset of glaucoma.

Glucocorticoids are also known to increase bone resorption and reduce bone formation in mammals (Turner et al. *Calcif Tissue Int.* 54: 311-5, 1995; Lane, N E et al. *Med Pediatr Oncol.* 41: 212-6, 2003). 11β-HSD-1 mRNA expression and reductase activity have been demonstrated in primary cultures of human osteoblasts in homogenates of human bone (Bland et al.; *J. Endocrinol.* 161: 455-464, 1999; Cooper et al.; *Bone,* 23: 119-125, 2000). In surgical explants obtained from orthopedic operations, 11β-HSD-1 expression in primary cultures of osteoblasts was found to be increased approximately 3-fold between young and old donors (Cooper et al.; *J. Bone Miner Res.* 17: 979-986, 2002). Glucocorticoids, such as prednisone and dexamethasone, are also commonly used to treat a variety of inflammatory conditions including arthritis, inflammatory bowl disease, and asthma. These steroidal agents have been shown to increase expression of 11β-HSD-1 mRNA and activity in human osteoblasts (Cooper et al.; *J. Bone Miner Res.* 17: 979-986, 2002). These studies suggest that 11β-HSD-1 plays a potentially important role in the development of bone-related adverse events as a result of excessive glucocorticoid levels or activity. Bone samples taken from healthy human volunteers orally dosed with the non-selective HSD½ inhibitor carbenoxolone showed a significant decrease in markers of bone resorption (Cooper et al.; *Bone.* 27: 375-81, 2000). Therefore, potent, selective 11β-HSD-1 inhibitors would treat, control, ameliorate, delay, or prevent the onset of conditions of glucocorticoid-induced or age-dependent osteoporosis.

In addition to the above, the following diseases, disorders and conditions also can be treated, controlled, prevented or delayed, by treatment with the compounds of the present invention: (1) hyperglycemia, (2) low glucose tolerance, (3) insulin resistance, (4) lipid disorders, (5) hyperlipidemia, (6) hypertriglyceridemia, (9) hypercholesterolemia, (10) low HDL levels, (11) high LDL levels, (12) atherosclerosis and its sequelae, (13) vascular restensosis, (14) pancreatitis, (15) abdominal obesity, (16) neurodegenerative disease, (17) retinopathy, (18) nephropathy, (19) neuropathy, (20) hypertension and other disorders where insulin resistance is a component, and (21) other diseases, disorders, and conditions that can benefit from reduced local glucocorticoid levels.

Biological Data

Measurement of Inhibition Constants:

The ability of test compounds to inhibit human 11β-HSD-1 enzymatic activity in vitro was evaluated in a Scintillation Proximity Assay (SPA). Tritiated-cortisone substrate, NADPH cofactor, and titrated compound were incubated with truncated human 11β-HSD-1 enzyme (24-287AA) at room temperature to allow the conversion to cortisol to occur. The reaction was stopped by adding a non-specific 11β-HSD inhibitor, 18β-glycyrrhetinic acid. The tritiated cortisol was captured by a mixture of an anti-cortisol monoclonal antibody and SPA beads coated with anti-mouse antibodies. The reaction plate was shaken at room temperature and the radioactivity bound to SPA beads was then measured on a β-scintillation counter. The 11-βHSD-1 assay was carried out in 96-well microtiter plates in a total volume of 220 μl. To start the assay, 188 μl of master mix, which contained 17.5 nM $^3$H-cortisone, 157.5 nM cortisone, and 181 mM NADPH, was added to the wells. In order to drive the reaction in the forward direction, 1 mM G-6-P was also added. Solid compound was dissolved in DMSO to make a 10 mM stock followed by a subsequent 10-fold dilution with 3% DMSO in Tris/EDTA buffer (pH 7.4). Twenty-two μl of titrated compounds was then added in triplicate to the substrate. Reactions were initiated by the addition of 10 μl of 0.1 mg/ml *E. coli* lysates overexpressing 11β-HSD-1 enzyme. After shaking and incubating the plates for thirty minutes at room temperature, reactions were stopped by adding 10 μl of 1 mM glycyrrhetinic acid. The product, tritiated cortisol, was captured by adding 10 μl of 1 μM monoclonal anti-cortisol antibodies and 100 μl SPA beads coated with anti-mouse antibodies. After shaking for thirty minutes, plates were read on a liquid scintillation counter Topcount. Percent inhibition was calculated based on the background and the maximal signal. Wells that contained substrate without compound or enzyme were used as the background, while the wells that contained substrate and enzyme without any compound were considered as maximal signal. Percent of inhibition of each compound was calculated relative to the maximal signal and $IC_{50}$ curves were generated. This assay was applied to 11β-HSD-2 as well, whereby tritiated cortisol and $NAD^+$ were used as substrate and cofactor, respectively.

Compounds of the present invention are active in the 11-βHSD-1 assay described above and show selectivity for human 11-β-HSD-1 over human 11-β-HSD-2, as indicated in Table 1.

TABLE 1

| Compound | 11-β-HSD-1 and 11-β-HSD-2 activity | |
|---|---|---|
| | 11-β-HSD-1 IC$_{50}$ (nM) | 11-β-HSD-2 IC$_{50}$ (nM) |
| A | 51 | 8,280 |
| B | 29 | 5,270 |
| C | 73 | >10,000 |
| D | 203 | >30,000 |
| G | 95 | >8,750 |
| H | 778 | |
| I | 1030 | |
| J | 29 | 5,170 |
| K | 2000 | |
| L | 62 | >10,000 |
| M | 77 | 8,470 |
| N | 76 | 1,850 |
| O | 51 | 90,000 |
| P | 99 | 13,900 |
| R | 41 | 1,600 |
| S | 39 | 1,360 |

The data in Table 1 demonstrates that compounds A, B, C and D are active in the human 11β-HDS-1 enzymatic SPA assay described above and the tested compounds show selectivity for 11β-HSD-1 over 11β-HSD-1 inhibitors of this invention generally have an inhibition constant IC$_{50}$ of less than 5 µM and preferably less than 500 nM. Preferably, the compounds are selective, having an inhibition constant IC$_{50}$ against 11β-HSD-2 greater than 1000 nM and preferably greater than 10,000 nM. Generally, the IC$_{50}$ ratio for 11β-HSD-2 to 11β-HSD-1 of a compound is at least greater and preferably 100 or greater.

Synthetic Methods

The compounds and processes of the present invention can be better understood in connection with the following synthetic schemes, which illustrate the methods by which the compounds of the invention can be prepared. All substituents are as defined herein unless indicated otherwise. Starting materials can be obtained from commercial sources or prepared by well-established literature methods known to those of ordinary skill in the art.

The present invention is intended to encompass compounds having formula (I) as described herein when prepared by synthetic processes or by metabolic processes. Preparation of the compounds of the invention by metabolic processes includes those occurring in the human or animal body (in vivo) or processes occurring in vitro.

It is understood that the schemes described herein are for illustrative purposes only and that routine experimentation, including appropriate manipulation of the sequence of the synthetic route, protection of any chemical functionality that are not compatible with the reaction conditions, and deprotection at suitable points in the reaction sequence of the method are within the scope of the present invention. Suitable protecting groups and the methods for protecting and deprotecting different substituents using such suitable protecting groups are well know to those skilled in the art. Examples can be found in T. Greene and P. Wuts, Protecting Groups in Chemical Synthesis (3$^{rd}$ ed.), John Wiley & Sons, NY (1999), which is incorporated herein by reference in its entirety.

Scheme 1

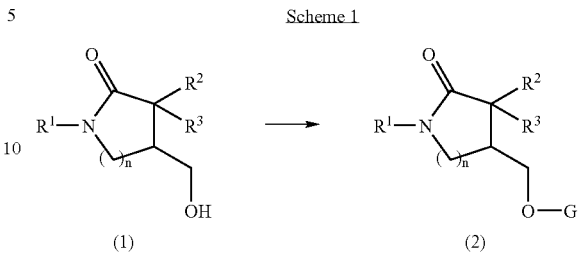

Compounds of formula (2) can generally be prepared by reacting an alcohol of formula (I) with a compound of formula G-W wherein W is an appropriate reactive leaving group such as, for example, sulfonyloxy group (e.g., 4-methylbenzesulfonyloxy, benzenesulfonyloxy, methanesulfonyloxy, trifluoromethanesulfonyloxy, and the like) or a halo group (e.g., Cl, Br, F, or I), wherein a halo group is preferred. The O-alkylation reaction can be conveniently carried out by mixing the reactants, in a reaction-inert solvent such as an ether (e.g., tetrahydrofuran, 1,4-dioxane, and the like), an aromatic solvent (e.g., benzene, toluene, xylene, chlorobenzene and the like), a dipolar aprotic solvent (e.g., N,N-dimethylamides of C$_{1-6}$ carboxylic acids such as N,N-dimethylformamide, N,N-dimethylacetamide, and the like, dimethysulfoxide, 1-methyl-2-pyrrolidinone, and the like), or any combination of solvents thereof. The addition of an appropriate base such as an alkali metal hydride or alkoxide can be used to deprotonate the hydroxyl group and enhance the rate of the reaction. In some instances, it can be advantageous to conduct the reaction in the presence of a co-solvent such as hexamethylphosphoramide or 1,3-dimethyl-3,4,5,6-tetrahydro-2(1H)-pyrimidinone, which can be added to speed up the rate of the reaction. Alternatively, an organic base such as a tertiary amine (e.g., triethyl amine, diisopropylethyl amine, N-methylmorpholine, N-ethylmorpholine, 1,4-diazabicyclo[2.2.2]octane, 1,8-diazabicyclo[5.4.0]undec-7-ene, and the like), pyridine, an alkali metal or an earth alkaline metal carbonate, hydrogen carbonate, carboxylate, hydroxide or oxide, sodium carbonate, sodium hydrogen carbonate, potassium carbonate, sodium hydroxide, calcium oxide, sodium acetate, and the like, can optionally be used to pick up the acid that is formed during the course of the reaction. The reaction is generally conducted at about room temperature to an elevated temperature (e.g., 80-100° C.) depending on the choice of the leaving group, the presence or absence of the base, and the presence or absence of the co-solvent.

Alternatively, compounds of formula (2) can be obtained by treating alcohols of formula (I) with an alcohol of formula G-OH, in the presence of a mixture of triphenyl phosphine and an azodicarboxylate such as di-tert-butyl azodicarboxylate, diethyl azodicarboxylate, diisopropyl azodicarboxylate, and the like, and an anhydrous reaction-inert solvent at room temperature or below. Non-limiting examples of suitable reaction-inert solvent are an aliphatic hydrocarbon (e.g., hexane and the like), an aromatic solvent (e.g., toluene, xylene, benzene and the like), an ether (e.g., tetrahydrofuran, 1,4-dixoane and the like), and a dipolar solvent (e.g., N,N-dimethylformamide).

Scheme 2

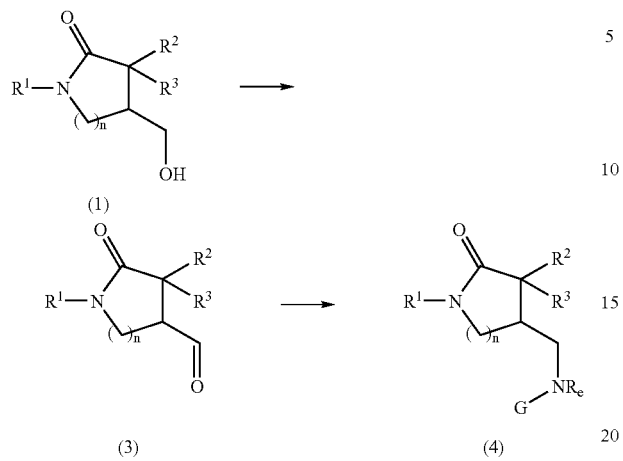

Compounds of formula (4) can be prepared from compounds of formula (I) as shown in Scheme 2. Compounds of formula (1) can be oxidized to aldehydes of formula (3) by treatment with an oxidizing agent such as Dess-Martin periodinane in a solvent (e.g., dichloromethane) at about room temperature.

Compounds of formula (4) wherein $R_e$ is hydrogen or methyl can be prepared from reductive amination of aldehydes of formula (3). Reductive amination can be carried out by reducing a mixture of the reactants in the presence of a reducing agent and an amine of formula $HNR_e$-G, wherein $R_e$ is hydrogen or methyl in a suitable reaction-inert solvent. In particular, the reaction mixture can be stirred and/or heated in order to facilitate the reaction. Suitable solvents, for example, include esters (e.g., ethyl acetate, isopropyl acetate, and the like), ethers (e.g., tetrahydrofuran, diethylether, 1,4-dioxane, and the like), halogenated hydrocarbons (e.g., dichloromethane, trichloromethane, and the like), dipolar aprotic solvents (e.g., N,N-dimethylformamide, dimethylsulfoxide and the like), or a mixture of solvents thereof. Non-limiting examples of reducing agents include cyanoborohydride, sodium borohydride, sodium triacetoxyborohydride, or hydrogen (optionally conducted at an increased pressure) in the presence of an appropriate catalyst such as palladium-on-carbon, platinum-on-carbon, and the like. Sources of hydrogen include gaseous hydrogen, formic acid, cyclodienes such as cyclohexyldiene, or a salt of formic acid such as ammonium formate. While borohydride is used as a reducing agent, it can be advantageous to conduct the reaction in the presence of an acid such as, but not limited to, acetic acid, hydrochloric acid, or 4 A molecular sieve.

Compounds of formula (4), wherein $R_e$ is hydrogen, can be converted to compounds of formula (4), wherein $R_e$ is alkyl or haloalkyl, by the process of N-alkylation with compounds having formula $R_e$-W wherein W is as defined herein. The alkylation can be carried out by mixing the reactants, optionally in a reaction-inert solvent such as an aromatic solvent (e.g., benzene, toluene, xylenes, and the like), an ester of $C_{1-6}$ carboxylic acids (e.g., ethyl acetate, isopropyl acetate and the like), a ketone (e.g., 2-propanone, acetone, and the like), an ether (e.g., tetrahydrofuran, 1,4-dioxane, dimethyl ether, tert-butyl methyl ether, and the like), a dipolar aprotic solvent (e.g., N,N-dimethylformamide, N,N-dimethylacetamide, dimethylsulfoxide and the like), or a mixture of solvents thereof. The addition of an appropriate base such as an alkali metal, an earth alkaline metal carbonate, hydrogen carbonate, hydroxide, oxide, carboxylate (e.g., sodium carbonate), sodium hydrogen carbonate, potassium carbonate, sodium hydroxide, lithium hydroxide, calcium oxide, sodium acetate, and the like), or an organic base such as pyridine or a tertiary amine (e.g., triethylamine, diisopropylethylamine, N-methylmorpholine, 1,8-diazabicyclo[5.4.0]undec-7-ene, and the like) can optionally be used to pick up the acid formed during the reaction. The reaction is conducted at about room temperature or at an elevated temperature.

Scheme 3

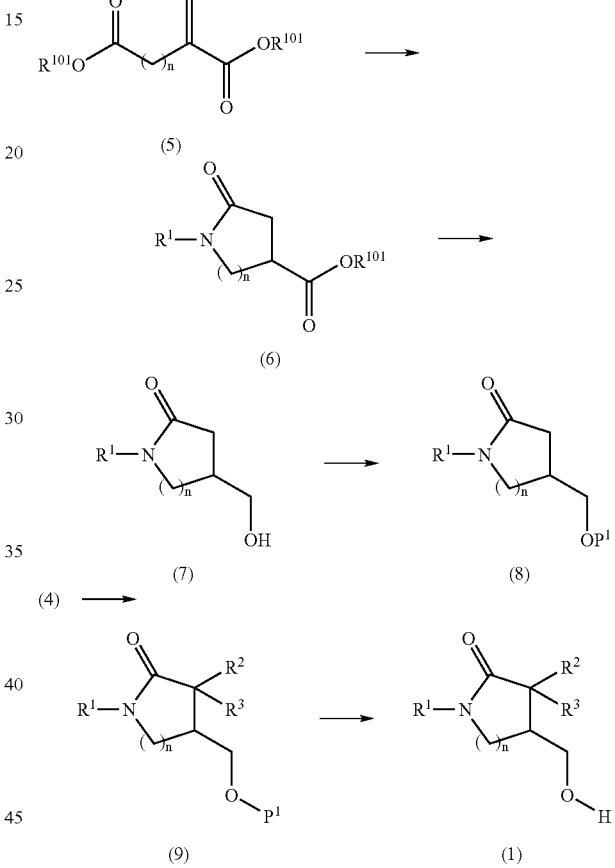

Compounds of formula (I) can be prepared from compounds of formula (5) wherein $R^{101}$ is $C_{1-6}$ alkyl as shown in Scheme 3. When treated with an amine of formula $R^1NH_2$ in a solvent such as $C_{1-6}$ alcohol (for example, methanol, ethanol, 1-butanol, and the like) at an elevated temperature (for example, 50-100° C., preferably 60-90° C.), compounds of formula (5) cyclized to provide lactams of formula (6).

Reduction of compounds of formula (6) provides alcohols of formula (7). The reduction reaction can be accomplished by stirring compounds of formula (6) with an appropriate reducing agent, in a solvent such as methanol, or aromatic solvent such as toluene, at room temperature, and if desired, heating the reactants in an appropriate solvent. Non-limiting examples of suitable reducing agents include, but are not limited to, sodium borohydride, diisobutyl aluminium hydride, lithium aluminum hydride, and the like.

Compounds of formula (7) are protected by treating with trialkylsilyl halides of formula $(R^{12})_3SiX$ (wherein X is Cl, Br, or I and each $R^{102}$ is independently $C_{1-6}$ alkyl (preferably tert-butyldimethylsilyl chloride)) in the presence of imidazole, and in a solvent such as N,N-dimethylformamide. As a result, compounds of formula (8) wherein $P^1$ is —Si($R^{102}$)$_3$ are provided.

Compounds of formula (8) can be mono- to provide compounds of formula (9) wherein one of $R^2$ and $R^3$ is hydrogen or bis-alkylated to provide compounds of formula (9), wherein both $R^2$ and $R^3$ are other than hydrogen. Bis-alkylation can be achieved sequentially or in a one-pot operation.

Mono or bis-alkylation of esters of general formula (11) can be achieved in the presence of a base such as, but not limited to, a metal hydride (e.g., sodium hydride, potassium hydride and the like) or a metal alkoxide (e.g., sodium methoxide, sodium ethoxide, and the like) and an alkylating agent such as, but not limited to, alkyl halides (e.g., methyl iodide, allyl bromide and the like). The reaction is generally performed in a solvent such as, but not limited to, anhydrous N,N-dimethylformamide and at a temperature from about 0° C. to about 23° C.

Removal of the protecting group $P^1$ can be achieved to provide compounds of formula (1). This can be accomplished by stirring with an acid (e.g., hydrochloric acid and the like) or tetrabutylammonium fluoride, in a solvent such as $C_{1-6}$ alcohol (e.g., methanol, ethanol and the like), an ether (e.g., tetrahydrofuran and the like), or a haloalkane (e.g., dichloromethane, chloroform, dichloroethane and the like) at ambient temperature.

of a small amount of N,N-dimethylformamide, in a solvent, at about room temperature to about 60° C.) in a solvent such as a haloalkane (e.g., dichloromethane, chloroform, and the like) ether (e.g., tetrahydrofuran, diethyl ether, and the like), or esters (e.g., ethyl acetate, isopropyl acetate and the like) in the presence of 4-dimethylaminopyridine and an organic base (e.g., a tertiary amine (diisopropylethylamine, triethylamine, pyridine, and the like)), at a temperature of about room temperature and below.

Rearrangement of compounds of formula (12) in the presence of a base such as potassium bis(trimethylsilyl)amide, in a solvent such as an aromatic hydrocarbon (e.g., toluene, xylene, and the like), followed by treatment with trimethylsilyl chloride, provides compounds of formula (13).

Esterification of compounds of formula (13) affords esters of formula (14). The transformation to a methyl ester can be achieved by stirring with trimethylsilyl diazomethane in a solvent (such as, but not limited to, a mixture of an aromatic solvent (e.g. toluene, xylene, benzene, and the like)) and methanol, at about room temperature. Conversion to esters of formula (4) wherein $R^{101}$ is $C_{1-6}$ alkyl can be accomplished by stirring the acid of formula (13) with thionyl chloride, optionally in the presence of catalytic amount of N,N-dimethylformamide, at about room temperature to about 70° C., in a $C_{1-6}$ alcohol (e.g., methanol, ethanol, isopropyl alcohol, n-butanol, and the like).

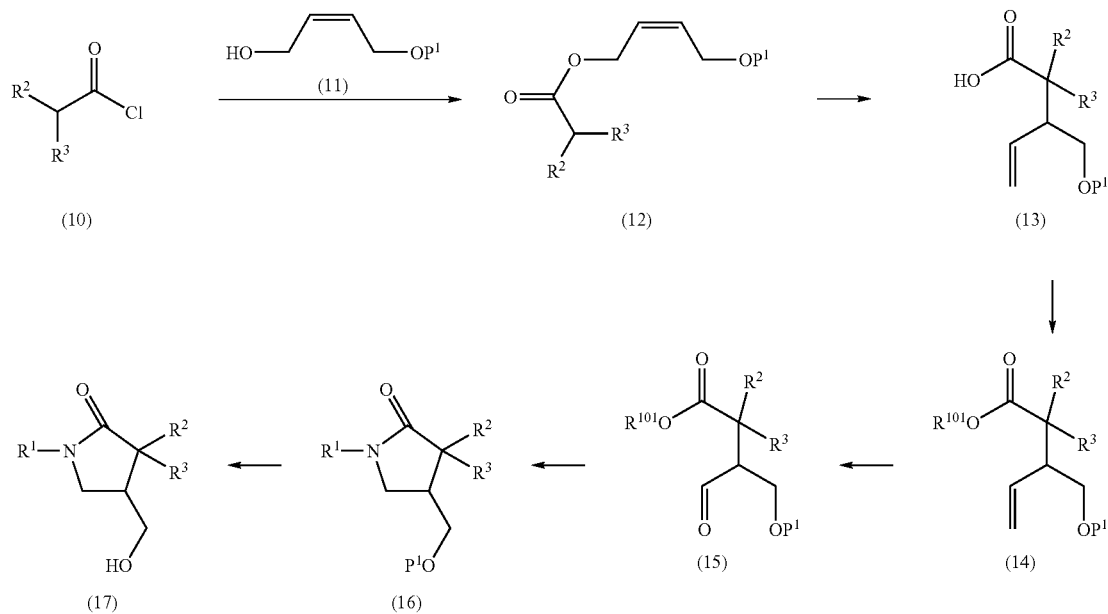

Scheme 4

Compounds of formula (17) can also be prepared from but-2-ene-1,4-diol as shown in Scheme 4. Mono-protection of but-2-ene-1,4-diol to provide compounds of formula (11) wherein $P^1$ is trialkyl silyl, in particular $P^1$ is tert-butyldimethylsilyl, can be performed using reaction conditions as described in the conversion of (7) to (8) in Scheme 3.

Reaction of compounds of formula (11) with acid chlorides of formula (10) (purchased or prepared in situ by treatment of the corresponding acids with a chlorinating agent such as thionyl chloride, or oxalyl chloride, optionally in the presence Compounds of formula (15) can be prepared by reacting compounds of formula (14) with ozone following art-known ozonolysis procedures. Cyclization of compounds of formula (15) in the presence of an amine of formula $R^1NH_2$ in a solvent such as an ether (e.g., tetrahydrofuran and the like) at about room temperature, and a reducing agent such as, but not limited to, sodium cyanoborohydride, sodium triacetoxyborohydride, and the like, optionally in the presence of a dehydrating agent such as, but not limited to, a 4A molecular sieve and the like, or an acid such as acetic acid, provide pyrrolidinones of formula (16).

EXAMPLE 1

6-[(1-cycloheptyl-4,4-dimethyl-5-oxopyrrolidin-3-yl)methoxy]nicotinonitrile

EXAMPLE 1A

1-Cycloheptyl-5-oxo-pyrrolidine-3-carboxylic acid methyl ester

A solution of dimethyl itaconate (0.5 g, 3.16 mmoles), cycloheptylamine (0.357 g, 3.16 mmoles) in methanol (5 mL) was heated at 85° C. for eighteen hours. The solvent was evaporated in vacuo and the resulting crude product was purified by flash chromatography (hexanes/ethyl acetate 80:20 to 20:80) to give the title compound as a colorless oil.

EXAMPLE 1B 4-(tert-Butyl-dimethyl-silanyloxymethyl)-1-cycloheptyl-pyrrolidine-2-one Sodium borohydride (0.213 g, 5.77 mmoles) was added to a solution of Example 1A (0.7 g, 2.92 mmoles) in methanol (3 mL) and tetrahydrofuran (3 mL) and stirred at 60° C. for two hours. The reaction was cooled to 0° C. and O-phosphoric acid (1.6 g, 17.4 mmoles) was added and stirred. The reaction was filtered through a pad of celite, rinsed with methanol, and concentrated under vacuo. The crude oil was taken up in ethyl acetate (25 mL) and washed with water (25 mL). The organic layer was dried with $MgSO_4$, filtered and evaporated in vacuo. The resulting oil was taken up in N,N-dimethylformamide (4 mL) and imidazole (391 g, 5.76 mmoles) and Tert-butyl-chloro-dimethyl-silane (583 g, 3.88 mmoles) were added and stirred for three hours. The reaction was diluted with ethyl acetate (40 mL) and washed with water (50 mL) and brine (25 mL). The organic layer was dried with $MgSO_4$ filtered and evaporated in vacuo. The crude product was purified by flash chromatography (hexanes:ethyl acetate 95:5 to 75:25) to give the title compound as a colorless oil.

EXAMPLE 1C 4-(tert-Butyl-dimethyl-silanyloxymethyl)-1-cycloheptyl-3-methyl-pyrrolidin-2-one A solution of Example 1B (1.09 g, 3.07 mmoles) in tetrahydrofuran (3.5 mL) was added drop wise to a solution of lithium bis(trimethylsilyl)amide in tetrahydrofuran (3.7 mL, 3.7 mmoles) at room temperature and stirred for two hours at that temperature. A solution of methyl iodide (0.54 g, 3.83 mmoles) in tetrahydrofuran (1 mL) was added drop wise to the reaction mixture at room temperature and stirred for another two hours. The reaction was quenched with 10% $NH_4Cl$ (25 mL) and extracted with ethyl acetate. The organic layer was washed with brine (25 mL), dried with $MgSO_4$, filtered, and solvent evaporated in vacuo. The crude product was purified by flash column chromatography (hexanes:ethyl acetate 95:5 to 60:40) to provide the title compound.

EXAMPLE 1D 4-(tert-Butyl-dimethyl-silanyloxymethyl)-1-cycloheptyl-3,3-dimethyl-pyrrolidin-2-one Butyl lithium (1.28 mL, 0.88 mmoles) in hexanes was added to a solution of dimethyl amine (64 mg, 0.88 mmoles) in tetrahydrofuran (2.5 mL) at −78° C. The reaction was stirred at that temperature for twenty minutes and then Example 1D (0.25 g, 0.737 mmoles) in tetrahydrofuran was added. The reaction was slowly warmed to room temperature and stirred for one hour. A solution of methyl iodide (0.209 g, 1.47 mmoles) in tetrahydrofuran (1 mL) was added drop wise to the reaction and stirred for another eight hours. The reaction was quenched with 10% $NH_4Cl$ and extracted with ethyl acetate. The organic layer was washed with brine (25 mL), dried with $MgSO_4$, filtered, and evaporated in vacuo. The crude product was purified by flash column chromatography (hexanes:ethyl acetate 95:5 to 70:30) to provide the title compound as a colorless oil.

EXAMPLE 1E

6-[(1-cycloheptyl-4,4-dimethyl-5-oxopyrrolidin-3-yl)methoxy]nicotinonitrile

Two drops of 12M HCl was added to a solution of Example 1D (75 mg, 0.2 mmoles) in methanol (1 mL) and stirred for one hour at room temperature. The solvent was evaporated in vacuo. The resulting oil was taken in N,N-dimethylformamide (1 mL) and 60% NaH (15 mg, 0.27 mmoles) was added, which was followed by 6-chloronicotinonitrile (35 mg, 0.25 mmoles). The reaction was stirred at room temperature for two hours and quenched with 10% $NH_4Cl$. The product was extracted with ethyl acetate and washed with water (4 mL). The organic layers were evaporated in vacuo and the crude reaction mixture was purified by preparative reverse phase HPLC on a Waters Symmetry C8 column (25 mm×100 mm, 7 μm particle size) using a gradient of 20% to 100% acetonitrile:water (0.1% trifluoroacetic acid) over eighteen minutes at a flow rate of 40 mL/minute to provide the title compound as the trifluoroacetic acid salt. $^1H$ NMR (300 MHz, $CDCl_3$) δ ppm 8.48 (dd, J=2.33, 0.64 Hz, 1H), 7.80 (dd, J=8.66, 2.33 Hz, 1H), 6.82 (dd, J=8.66, 0.78 Hz, 1H), 4.50 (dd, J=10.87, 6.04 Hz, 1H), 4.36 (dd, J=10.86, 8.24 Hz, 1H), 4.03-4.19 (m, 1H), 3.46 (dd, J=9.85, 7.64 Hz, 1H), 3.08 (dd, J=9.87, 7.94 Hz, 1H), 2.45 (qd, J=7.94, 6.01 Hz, 1H), 1.43-1.82 (m, 12H), 1.24 (s, 3H), 1.06 (s, 3H). MS ($APCI^+$) m/z 342.2 $(M+H)^+$.

EXAMPLE 2

4-(4-{[(5-cyanopyridin-2-yl)oxy]methyl}-3,3-dimethyl-2-oxopyrrolidin-1-yl)azepane-1-carboxamide

EXAMPLE 2A

4-Amino-azepane-1-carboxylic acid tert-butyl ester

A solution of N-(tert-butoxycarbonyl)-hexahydro-1H-azepin-4-one (0.5 g, 2.34 mmoles), O-benzylhydroxylamine hydrochloride (0.41 g, 2.57 mmoles) and ammonium acetate (0.45 g, 5.86 mmoles) in methanol (10 mL) was refluxed for 1.2 hours. The solvent was evaporated in vacuo and the crude oxime was purified by flash column chromatography (hexanes:ethyl acetate 100:0 to 50:50). The product was taken in 4N $NH_3$ in methanol (10 mL) and added 10% by weight Pd/C (100 mg) and stirred over $H_2$ at balloon pressure for twelve hours. The reaction was filtered through a pad of celite and filtrate evaporated in vacuo to provide the title compound.

EXAMPLE 2B

Isobutyric acid 4-(tert-butyl-dimethyl-silanyloxy)but-2-enyl ester

A solution of 60% NaH (2.27 g, 56.75 mmoles) in tetrahydrofuran (15 mL) was cooled to 0° C. and to the solution cis-2-butene-1,4-diol (5.0 g, 56.75 mmoles) in tetrahydrofuran (10 mL) was added. The reaction was stirred at room temperature for thirty minutes and tert-butyl-chloro-dimethyl-silane (8.56 g, 56.75 mmoles) in tetrahydrofuran (15 mL) was added and stirred for another two hours. The reaction was quenched with 10% $NH_4Cl$ and extracted with ethyl acetate. The organic layer was washed with brine (30 mL), dried with $MgSO_4$, filtered, and evaporated in vacuo. The crude oil was purified by flash column chromatography (hexanes:ethyl acetate 100:0 to 50:50). The resulting product was dissolved in dichloromethane (25 mL) and pyridine (3.95 g, 50.6 mmoles) and isobutyryl chloride (2.68 g, 25.3 mmoles) were added. Then, the solution was stirred at room temperature for twelve hours. The reaction was quenched with water and extracted with dichloromethane. The organic layer was washed with water (50 mL), dried with $MgSO_4$, filtered and evaporated in vacuo. The solvent was evaporated in vacuo and the product was purified by flash column chromatography (hexanes:ethyl acetate 100:0 to 70:30) to provide the title compound as a colorless oil.

EXAMPLE 2C 3-(tert-butyl-dimethyl-silanyloxymethyl)-2,2-dimethyl-pent-4-enoic acid methyl ester A solution of potassium bis(trimethylsilyl)amide (44 mL, 22 mmoles) in Toluene was cooled to −78° C. To the solution, Example 2B (4.0 g, 14.7 mmoles) in Toluene (15 mL) was added drop wise. The reaction was stirred for forty-five minutes and chloro trimethylsilane (3.19 g, 29.4 mmoles) was added and the reaction was warmed to 80° C. for 1.5 hours. The reaction was quenched with 10% $NH_4Cl$ (50 mL) and extracted with ethyl acetate. The organic layer was washed with brine (30 mL), dried with $MgSO_4$, filtered, and evaporated in vacuo. The resulting oil was dissolved in ethyl acetate (25 mL) and methanol (5 mL) and (trimethylsilyl)diazomethane (35 mL, 70 mmoles) was added. The reaction was stirred at room temperature for two hours. The solvent was evaporated in vacuo and the crude product was purified by flash column chromatography (hexanes:ethyl acetate 100:0 to 60:40) to provide the title compound as a colorless oil.

EXAMPLE 2D 3-(tert-butyl-dimethyl-silanoxymethyl)-2,2-dimethyl-4-oxo-butyric acid methyl ester A solution of Example 2C (3.5 g, 12.2 mmol)in dichloromethane (25 mL) and methanol (2.5 mL) was cooled to −78° C. and $O_3$ was bubbled for twenty-five minutes. The reaction was purged with $N_2$ and DMS (5.29 g, 85.4 mmol) was added. The reaction was stirred at room temperature for three hours. The solvent was evaporated in vacuo and the product purified by flash column chromatography (hexanes: ethyl acetate) 100:0 to 50:50) to provide the title compound as an oil.

EXAMPLE 2E

4-[4-(tert butyl-dimethyl-silanyloxymethyl)-3,3-dimethyl-2-oxo-pyrrolidin-1-yl]-azepane-1-carboxylic acid tert buty; ester A solution of Example 2A (0.2 g, 0.95 mmoles), Example 2D (0.25 g, 0.86 mmoles), and MP-triacetoxyborohydride (MP-TABH) (700 mg, 1.6 mmoles) in tetrahydrofuran (2.5 mL) was stirred for twelve hours. The reaction was filtered and evaporated in vacuo. The residue was taken in Toluene and heated at 90° C. for three hours. The solvent was evaporated in vacuo and the product was purified by flash column chromatography (dichloromethane:methanol 95:5) to provide the title compound.

EXAMPLE 2F

4-[4-(5-cyano-pyridin-2-yloxymethyl)-3,3-dimethyl-2-oxo-pyrrolidin-1-yl]-azepane-1-carboxylic acid tert-butyl ester Tetrabutyl ammonium fluoride (0.127 g, 0.48 mmoles) was added to Example 2E (0.177 g, 0.4 mmoles) in tetrahydrofuran (1.5 mL) and stirred for two hours at room temperature. The reaction was partitioned between ethyl acetate (5 mL) and water (3 mL). The organic phase was dried with $MgSO_4$, filtered, and evaporated in vacuo. The residue was taken in N,N-dimethylformamide (2.5 mL) and 60% NaH (24 mg, 0.6 mmoles) and 6-chloronicotinonitrile (69 mg, 0.5 mmoles) were added and stirred for three hours. The reaction was quenched with 10% $NH_4Cl$ and extracted with ethyl acetate. The organic phase was dried with $MgSO_4$, filtered, and evaporated. The resulting crude product was purified by flash column chromatography (hexanes:ethyl acetate 75:25 to 25:75) to provide the title compound.

EXAMPLE 2G 4-(4-{[(5-cyanopyridin-2-yl)oxy]methyl}-3,3-dimethyl-2-oxopyrrolidin-1-yl)azepane-1-carboxamide Trifluoroacetic acid (0.75 mL) was added to a solution of Example 2F (0.108 g, 0.24 mmoles) in dichloromethane (0.75 mL) and stirred for one hour. The solvent was evaporated in vacuo. The residue was taken in dichloromethane (1.5 mL) and cooled to −78° C. Triphosgene (24 mg, 0.08 mmoles) was added and stirred for one hour. To the reaction, $NH_4OH$ (1 mL) was added and stirred at room temperature for one hour. The product was extracted with dichloromethane, dried with $MgSO_4$, filtered, and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% trifluoroacetic acid) over eighteen minutes at a flow rate of 40 mL/minute to provide the title compound. $^1$H NMR (300 MHz, $CDCl_3$) δ ppm 8.48 (dd, J=2.33, 0.64 Hz, 1H), 7.80 (dd, J=8.66, 2.33 Hz, 1H), 6.82 (dd, J=8.66, 0.78 Hz, 1H), 5.81 (b,r, 2H), 4.50 (dd, J=10.87, 6.04 Hz, 1H), 4.36 (dd, J=10.86, 8.24 Hz, 1H), 4.03-4.19 (m, 1H), 3.16 (m, 4H), 3.46 (dd, J=9.85, 7.64 Hz, 1H), 3.08 (dd, J=9.87, 7.94 Hz, 1H), 2.45 (qd, J=7.94, 6.01 Hz, 1H), 1.43-1.82 (m, 6H), 1.24 (s, 3H), 1.06 (s, 3H). MS (APCI+) m/z 386.2 $(M+H)^+$.

EXAMPLE 3

1-cycloheptyl-3,3-dimethyl-4-(phenoxymethyl)pyrrolidin-2-one

EXAMPLE 3A

1-Cycloheptyl-4-hydroxymethyl-3,3-dimethyl-pyrrolidin-2-one

Two drops of 12M HCl was added to a solution of Example 1D (75 mg, 0.21 mmoles) in methanol (1.25 mL) and stirred for one hour at room temperature. The solvent was evaporated in vacuo to provide the title compound as a colorless oil.

EXAMPLE 3B 1-cycloheptyl-3,3-dimethyl-4-(phenoxymethyl)pyrrolidin-2-one

A solution of Example 3A (50 mg, 0.2 mmoles), phenol (23.5 mg, 0.25 mmoles), and triphenyl phosphine (85.8 mg, 0.33 mmoles) was stirred in anhydrous Toluene (1.25 mL). To the reaction, di-tert-butyl azodicarboxylate (76.9 mg, 0.33 mmoles) was added and heated to 80° C. for one hour. The reaction mixture was partitioned between toluene and water. The organic phase was separated and solvent evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% trifluoroacetic acid) over eighteen minutes at a flow rate of 40 mL/minute to provide the title compound. $^1$H NMR (500 MHz, CDCl$_3$) δ ppm 7.27-7.32 (m, 2H), 6.95-6.99 (m, 1H), 6.88-6.91 (m, 2H), 4.06-4.19 (m, 1H), 4.07 (dd, J=9.15, 5.65 Hz, 1H), 3.92 (t, J=8.77 Hz, 1H), 3.51 (dd, J=9.92, 7.63 Hz, 1H), 3.13 (dd, J=9.76, 7.78 Hz, 1H), 2.45 (qd, J=7.86, 5.72 Hz, 1H), 1.43-1.82 (m, 12H), 1.25 (s, 3H), 1.05 (s, 3H). MS (APCI+) m/z 316.2 (M+H)$^+$.

EXAMPLE 4

1-cycloheptyl-4-{[(2-fluorophenyl)(methyl)amino]methyl}-3,3-dimethylpyrrolidin-2-one

EXAMPLE 4A

1-Cycloheptyl-4,4-dimethyl-5-oxo-pyrrolidine-3-carbaldehyde

To a solution of Example 1D (0.168 mg, 0.475 mmoles) in methanol (1.5 mL), two drops of 12M HCl was added and stirred for one hour. The solvent was evaporated in vacuo. The residue was taken in dichloromethane (2.5 mL) and Dess-Martin periodinane (0.25 gm, 0.593 mmoles) was added and stirred at room temperature for two hours. The reaction was quenched with 10% sodium bisulfite and extracted with dichloromethane. The organic phase was washed with water, dried with MgSO$_4$, filtered, and evaporated in vacuo to provide the title compound.

EXAMPLE 4B 1-cycloheptyl-4-{[(2-fluorophenyl)(methyl)amino]methyl}-3,3-dimethylpyrrolidin-2-one A solution of Example 4A (30 mg, 0.12 mmoles), 2-fluoro-N-methylaniline (19 mg, 0.15 mmoles) MP-triacetoxyborohydride (137 mg, 0.3 mmoles) in tetrahydrofuran (1.25 mL) was stirred for twelve hours. The reaction was filtered and solvent evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% trifluoroacetic acid) over eighteen minutes at a flow rate of 40 mL/minute to provide the title compound. $^1$H NMR (500 MHz, CDCl$_3$) δ ppm 6.90-7.10 (m, 4H), 4.01-4.13 (m, 1H), 3.32 (dd, J=9.88, 7.50 Hz, 1H), 3.11-3.21 (m, 2H), 3.09 (t, J=9.36 Hz, 1H), 2.83 (s, 3H), 2.17-2.27 (m, 1H), 1.59-1.70 (m, 6H), 1.45-1.57 (m, 6H), 1.16 (s, 3H), 0.95 (s, 3H). MS (APCI+) m/z 347.2 (M+H)$^+$.

EXAMPLE 5

6-{[1-(5-hydroxycyclooctyl)-4,4-dimethyl-5-oxopyrrolidin-3-yl]methoxy}nicotinonitrile

EXAMPLE 5A 5-(tert-Butyl-dimethyl-silanyloxy)-cyclooctanol

Sodium bis(trimethylsilyl)amide (76.27 mL, 1 M in tetrahydrofuran, 76.27 mmol) was added drop wise to a stirred and cooled (0° C.) solution of cyclooctane-1,5-diol (10 g, 69.34 mmol) in dry tetrahydrofuran (120 mL). After the addition, the resulting solution was warmed to room temperature and stirred for another thirty minutes. The solution was re-cooled (0° C.) and a solution of tert-butyl-chloro-dimethyl-silane (10.45 g, 69.34 mmol) in tetrahydrofuran (20 mL) was added drop wise. The solution was then warmed to room temperature and stirred overnight before an NH$_4$Cl solution was added. The mixture was partitioned with diethyl ether, and the organic phase was washed with brine, dried (MgSO$_4$), filtered, and evaporated. The residue was purified over silica gel using 2-40% ethyl acetate in hexanes to provide the title compound as an oil.

EXAMPLE 5B 5-(tert-Butyl-dimethyl-silanyloxy)-cyclooctanone

Tetrapropylammonium perruthenate (0.82 g, 2.43 mmol) was added to a stirred and cooled (0° C.) solution of Example 5A (12.11 g, 46.90 mmol), 4-methylmorpholine N-oxide (8.24 g, 70.35 mmol), and 4 Å molecular sieves (23 g) in dry dichloromethane (120 mL). After the addition, the mixture was warmed to room temperature and stirred for another three hours. The black mixture was filtered through a pad of Celite and the solvent was evaporated. The residue was purified over silica gel using 5-50% ethyl acetate in hexanes to give the title compound as an oil.

EXAMPLE 5C 5-(tert-Butyl-dimethyl-silanyloxy)-cyclooctylamine

Example 5B (3.59 G, 14.01 mmol), ammonium acetate (10.80 g, 140.13 mmol), and sodium cyanoborohydride (3.52 g, 56.04 mmol) were stirred in methanol (50 mL) for twelve hours. The solvent was evaporated and the residue was partitioned with dichloromethane and water. The organic phase was washed with NaHCO$_3$ solution brine, dried (Na$_2$SO$_4$), filtered, and evaporated. The crude amine was used in the following step without further purification.

EXAMPLE 5D

5-Amino-cyclooctanol

Benzyl chloroformate (4 mL, 28.02 mmol) was added to a stirred and cooled (0° C.) solution of the product of Example 5C (14.01 mmol) and diisopropylethyl amine (7.5 mL, 42.03 mmol) in dry dichloromethane (50 mL). After the addition, the solution was warmed to room temperature and stirred for another three hours. It was quenched with NaHCO$_3$ solution. The phases were separated and the organic phase was washed with NaHSO$_4$ solution brine, dried (Na$_2$SO$_4$), filtered, and evaporated. The crude [5-(tert-Butyl-dimethyl-silanyloxy)-cyclooctyl]-carbamic acid benzyl ester was isolated as an oil and was used without further purification. Tetrabutyl ammonium fluoride (42 mL, 1 M in tetrahydrofuran, 42.03 mmol) was added to a solution of crude [5-(tert-Butyl-dimethyl-silanyloxy)-cyclooctyl]-carbamic acid benzyl ester (about 14.01 mmol) in tetrahydrofuran (35 mL). The resulting solution was stirred for two hours at 23° C. before it was partitioned with diethyl ether and water. The organic layer was washed with brine, dried (MgSO$_4$), filtered, and evaporated. The residue was purified over silica gel using 5-50% ethyl acetate in hexanes to give (5-Hydroxy-cyclooctyl)-carbamic acid benzyl ester as an oil. (5-Hydroxy-cyclooctyl)-carbamic acid benzyl ester (2.68 g, 9.66 mmol) was stirred in the presence of Pd(OH)$_2$/C (0.5 g) in methanol under H$_2$ (balloon) for two hours at 23° C. before it was filtered through a pad of Celite and the solvent was evaporated. The title compound was isolated as an oil and used without further purification.

EXAMPLE 5E

4-(tert-Butyl-diphenyl-silanyloxy)-but-2-en-1-ol

NaH (3 g, 75 mmol, 60% in oil) was added portion-wise to a stirred and cooled (0° C.) solution of but-2-ene-1,4-diol (6 g, 68.09 mmol) in dry tetrahydrofuran (250 mL). After the addition, the mixture was allowed to warm to room temperature and stirred for another two hours. The resulting white mixture was then cooled (0° C.) and tert-butyl-chlorodiphenylsilane (15.7 mL, 61.28 mmol) was added drop wise. After twenty minutes, the cooling bath was removed and the mixture was allowed to stir overnight at room temperature. Saturated NH$_4$Cl was poured into the reaction mixture and the reaction was partitioned with diethyl ether (200 mL). The organic layer was washed with brine, dried (MgSO$_4$), and filtered. The resulting oil was used in the following step without further purification.

EXAMPLE 5F

Isobutyric acid 4-(tert-butyl-diphenyl-silanyloxy)-but-2-enyl ester

Isobutyryl chloride (10.4 mL, 98.04 mmol) was added drop wise to a stirred and a cooled (0° C.) solution of the product of Example 5E (61.28 mmol), diisopropylethyl amine (21.3 mL, 122.56 mmol), and 4-dimethylaminopyridine (0.30 g, 3.0 mmol) in dry dichloromethane (150 mL). The resulting solution was allowed to stir at 0° C. for five hours. After the completion of reaction (monitored by TLC), methanol (5 mL) was added to quench excess acid chloride. The solvent was removed under reduced pressure and the resulting slurry was partitioned using diethyl ether (200 mL) and saturated NH$_4$Cl (100 mL). The organic layer was washed successively with 20% NaHSO$_4$, NaHCO$_3$, brine, and it was dried over MgSO$_4$. After removal of solvent, the crude oil was purified over silica gel column using 10% diethyl ether in hexanes to give the title compound as a colorless oil: (20.5 g, 84% over 2 steps).

EXAMPLE 5G

3-(tert-Butyl-diphenyl-silanyloxymethyl)-2,2-dimethyl-pent-4-enoic acid

The product of Example 5F (15.26 g, 38.52 mmol) in dry toluene (30 mL) was added drop wise to a stirred and cooled (−78° C.) suspension of potassium bis(trimethylsilyl)amide (115 mL, 0.5 M in tol, 57.79 mmol) in dry toluene (100 mL). The resulting light yellow suspension was allowed to stir at −78° C. for one hour. Trimethylsilyl chloride (9.74 mL, 77.04 mmol) was then added drop wise to the mixture, and after ten minutes the resulting mixture was allowed to warm to room temperature. Afterwards, the mixture was heated at 80° C. for three hours. After cooling to room temperature, 20% NaHSO$_4$ was added and the reaction was partitioned with ethyl acetate. The organic phase was washed with brine and dried over MgSO$_4$. After the evaporation of solvent, the crude acid was purified over silica gel column using 20% diethyl ether in hexanes to give the title compound (14.4 g, 95%) as a white solid after standing at room temperature.

EXAMPLE 5H

3-(tert-Butyl-diphenyl-silanyloxymethyl)-2,2-dimethyl-pent-4-enoic acid methyl ester Trimethylsilyl diazomethane (29 mL, 2 M in hexanes, 57.78 mmol) was added to a stirred solution of Example 5G (15.58 g, 39.3 mmol) in toluene (100 mL) and methanol (20 mL). After one hour at room temperature, acetic acid (1.5 mL) was added to quench the excess reagent. The solvent was evaporated and the crude product was dissolved in diethyl ether and washed with NaHCO$_3$ solution brine, dried (MgSO$_4$), filtered, and evaporated. The title compound was isolated as an oil and used without further purification.

EXAMPLE 5I

4-(tert-Butyl-diphenyl-silanyloxy)-3-formyl-2,2-dimethyl-butric acid methyl ester Ozone was bubbled through a stirred and cooled (−78° C.) solution of Example 5H (11.5 g, 28.03 mmol) in a solution of dichloromethane (120 mL) and methanol (20 mL) with NaHCO$_3$ (4 g) and Sundan III (1 mg). Ozone was turned off after the red color of the dye turned to clear and the solution was purged with O$_2$ for thirty minutes. Me$_2$S (12.4 mL, 168 mmol) was added to the solution and the ice bath was removed to allow the solution to be warmed to room temperature and stirred for twelve hours. The reaction solution was filtered and the solvent was evaporated. The residue was purified over silica gel using 10% diethyl ether in hexanes to give the title compound as an oil.

EXAMPLE 5J

4-(tert-Butyl-diphenyl-silanyloxymethyl)-1-(5-hydroxy-cyclooctyl)-3,3-dimethyl-pyrrolidin-2-one The product of Example 5D (0.32 g, 2.22 mmol), the product of Example 5I (0.76 g, 1.85 mmol) and ground 4 Å molecular sieves (1 g) in dry tetrahydrofuran (15 mL) was stirred at room temperature for five hours. Sodium triacetoxyborohydride (1.2 g, 5.66 mmol) was added to the mixture and the reaction was allowed to stir at room temperature overnight. The resulting thick white suspension was filtered through a pad of Celite and the solvent was evaporated. The residue was redissolved in toluene (10 mL) and heated to 100° C. for two hours. The solvent was then evaporated and the residue was purified over silica gel using 10-50% ethyl acetate in hexanes to give the titled product as a thick oil.

EXAMPLE 5K 1-(5-Hydroxy-cyclooctyl)-4-hydroxymethyl-3,3-dimethyl-pyrrolidin-2-one Tetrabutyl ammonium fluoride (0.76 mL, 1 M in tetrahydrofuran, 0.76 mmol) was added to a stirred solution of the product of Example 5J (0.30 g, 0.60 mmol) in tetrahydrofuran (5 mL) at room temperature. The resulting solution was stirred for two hours and then partitioned with ethyl acetate and water. The organic phase was washed with brine, dried ($MgSO_4$), filtered, and evaporated. The residue was purified over silica gel using 20-100% ethyl acetate in hexanes to give the titled product as a white solid.

EXAMPLE 5L

6-{[1-(5-hydroxycyclooctyl)-4,4-dimethyl-5-oxopyrrolidin-3-yl]methoxy}nicotinonitrile NaH (25 mg, 0.594 mmol) was added in one portion to a stirred and cooled solution of the product of Example 5K (35 mg, 0.130 mmol) and 6-chloro-nicotinonitrile (60 mg, 0.435 mmol) in dry N,N-dimethylformamide (2 mL). After five hours of stirring at room temperature, the reaction was quenched with acetic acid (0.1 mL) and the mixture was purified on HPLC using $CH_3CN$/water 1% trifluoroacetic acid as eluent to provide the trifluoroacetic acid salt of the title compound as an oil. $^1$H NMR (300 MHz, $CD_3OD$) δ ppm 8.48 (dd, J=2.33, 0.64 Hz, 1H), 7.80 (dd, J=8.66, 2.33 Hz, 1H), 6.82 (dd, J=8.66, 0.78 Hz, 1H), 4.50 (dd, J=10.87, 6.04 Hz, 1H), 4.36 (dd, J=10.86, 8.24 Hz, 1H), 4.03-4.19 (m, 1H), 3.46 (dd, J=9.85, 7.64 Hz, 1H), 3.08 (dd, J=9.87, 7.94 Hz, 1H), 2.45 (qd, J=7.94, 6.01 Hz, 1H), 1.43-1.82 (m, 12H), 1.24 (s, 3H), 1.06 (s, 3H) MS (ESI+) m/z 354.0 (M–$H_2O$).

EXAMPLE 6

E-4-(4-{[(5-cyanopyridin-2-yl)oxy]methyl}-3,3-dimethyl-2-oxopyrrolidin-1-yl)adamantane-1-carboxamide

EXAMPLE 6A

E-4-Amino-adamantane-1-carboxylic acid

To 1.0 g (10 wt %) of 5% Pd/C is added 4-oxo-adamantane-1-carboxylic acid (10.0 g, 51.5 mmol) followed by 7M $NH_3$ in methanol (200 mL). The reaction mixture is stirred under an atmosphere of $H_2$ at 23° C. for 16-24 hours; water (200 mL) is added, and the catalyst is removed by filtration. The catalyst is washed with methanol and the filtrate solution is concentrated under reduced pressure at a bath temperature of 35° C. until the solvent stops coming over. Approximately 150 mL of a slurry remains. Acetonitrile (300 mL) is added to the slurry, which is then stirred for 3 hours at 23° C. The slurry is filtered and washed once with acetonitrile (100 mL). The wet cake is dried at 50° C. and 20 mmHg under $N_2$ to yield the title compound.

EXAMPLE 6B

E-4-Amino-adamantane-1-carboxylic acid methyl ester

Methanol (85 mL) was cooled to 0° C.; acetyl chloride (15.5 mL) was added drop wise; and then the solution was warmed to 23° C. for 15-20 minutes. Example 6A (8.53 g, 43.7 mmol) was added and the reaction solution was heated to 45° C. for sixteen hours. The reaction solution was cooled to 23° C. and acetonitrile (85 mL) was added. The reaction solution was concentrated under reduced pressure to ~¼ volume. The reaction solution was further chase distilled with acetonitrile (2×85 mL). The resulting suspension was cooled to 23° C. and filtered. The filtrate was recirculated twice to wash the wet cake. The product was dried at 50° C., 20 mmHg for sixteen hours to afford the title compound as a white crystalline solid.

EXAMPLE 6C

E-4-[4-(tert-Butyl-diphenyl-silanyloxymethyl)-3,3-dimethyl-2-oxo-pyrrolidin-1-yl]-adamantane-1-carboxylic acid methyl ester The product from Example 6B (4.9 g, 23.42 mmol), the product from Example 5I (8.88 g, 21.54 mmol), and ground 4 Å molecular sieves (10 g) in dry tetrahydrofuran (150 mL) were stirred at room temperature for five hours. Sodium triacetoxybrorohydride (11.41 g, 53.85 mmol) was added to the mixture and the reaction was allowed to stir at room temperature overnight. The resulting thick white suspension was filtered through a pad of Celite and the solvent was evaporated. The residue was redissolved in toluene (80 mL) and heated to 100° C. for two hours. The solvent was then evaporated and the residue was purified over silica gel using 10-50% ethyl acetate in hexanes to give the title compound as a thick oil.

EXAMPLE 6D

E-4-(4-Hydroxymethyl-3,3-dimethyl-2-oxo-pyrrolidin-1-yl)-adamantane-1-carboxylic acid methyl ester Tetrabutyl ammonium fluoride (29 mL, 1 M in tetrahydrofuran, 29 mmol) was added to a stirred solution of the product of Example 6C (10.59 g, 19.00 mmol) in tetrahydrofuran at room temperature. The resulting solution was stirred for two hours and then partitioned with ethyl acetate and water. The organic phase was washed with brine, dried ($MgSO_4$), filtered, and evaporated. The residue was purified over silica gel using 20-100% ethyl acetate in hexanes to give the titled product as a white solid.

EXAMPLE 6E

E-4-[4-(5-Cyano-pyridin-2-yloxymethyl)-3,3-dimethyl-2-oxo-pyrrolidin-1-yl]-adamantane-1-carboxylic acid methyl ester NaH (0.32 g, 60% in oil, 8.05 mmol) was added in one portion to a stirred and cooled (0° C.) solution of the product of Example 6D (1.50 g, 4.47 mmol) and 6-chloro-nicotinonitrile (1.11 g, 8.05 mmol) in tetrahydrofuran (10 ml) and 1,3-dimethyl-3,4,5,6-tetrahydro-2(1H)-pyrimidinone (10 mL). After the addition, the solution was warmed to room temperature and stirred for another five hours. The dark brown reaction mixture was cooled (0° C.) and quenched with acetic acid (0.5 mL) and partitioned with diethyl ether and water. The organic phase was washed with water and brine, dried (MgSO$_4$), filtered, and evaporated. The residue was purified over silica gel using 5-80% ethyl acetate in hexanes to give the title compound as a solid.

EXAMPLE 6F

E-4-[4-(5-Cyano-pyridin-2-yloxymethyl)-3,3-dimethyl-2-oxo-pyrrolidin-1-yl]-adamantane-1-carboxylic acid Potassium trimethylsilanolate (0.63 g, 4.93 mmol) was added in one portion to a stirred solution of the product of Example 6E (1.8 g, 4.11 mmol) in dry tetrahydrofuran (35 mL). The resulting solution was stirred overnight and then partitioned with diethyl ether and water. The organic phase was extracted with water and the combined water phase was acidified using NaHSO$_4$ to pH 1. The aqueous phase was extracted several times with ethyl acetate. The combined organic phase was then dried (MgSO$_4$), filtered, and evaporated. The resulting crude acid was isolated as a white solid and used in the following step without further purification.

EXAMPLE 6G

E-4-(4-{[(5-cyanopyridin-2-yl)oxy]methyl}-3,3-dimethyl-2-oxopyrrolidin-1-yl)adamantane-1-carboxamide 1-ethyl-3-[3-(dimethylamino)propyl]-carbodiimide hydrochloride (1.18 g, 6.16 mmol) was added in one portion to a stirred solution of the product of Example 6F (1.74 g, 4.11 mmol), 1-hydroxybenzotriazole hydrate (0.89 g, 6.57 mmol), and diisopropylethyl amine (2.15 mL, 12.33 mmol) in dry dichloromethane (10 mL). The resulting solution was stirred at room temperature for two hours before an ammonia solution (16.4 mL, 2 M in isopropanol, 32.8 mmol) was added. The resulting white suspension was stirred for one hour before it was diluted with dichloromethane (100 mL) and washed with 20% NaHSO$_4$ solution, 1 M NaOH, water, and brine. The solution was then dried (Na$_2$SO$_4$), filtered, and evaporated. The residue was purified over silica gel using 1-10% methanol in dichloromethane to give the title compound as a white solid. $^1$H NMR (300 MHz CDCl$_3$) δ ppm 1.09 (s, 3H) 1.25 (s, 3H) 1.51-1.74 (m, 2H) 1.80-2.18 (m, 9H) 2.34-2.66 (m, 3H) 3.37 (dd, J=9.49, 8.14 Hz, 1H) 3.76 (dd, J=9.66, 7.63 Hz, 1H) 3.87-3.96 (m, 1H) 4.39 (dd, J=10.85, 8.14 Hz, 1H) 4.48-4.61 (m, 1H) 5.23 (s, 1H) 5.56 (s, 1H) 6.83 (d, J=8.48 Hz, 1H) 7.81 (dd, J=8.48, 2.37 Hz, 1H) 8.48 (d, J=2.37 Hz, 1H). MS (ESI+) m/z 423.2 (M+H)$^+$.

EXAMPLE 7

9-(4-{[(5-cyanopyridin-2-yl)oxy]methyl}-3,3-dimethyl-2-oxopyrrolidin-1-yl)bicyclo [3.3.1]nonane-3-carboxamide

EXAMPLE 7A

9-Oxo-bicyclo[3.3.1]nonane-3-carboxylic acid methyl ester

3-Bromo-2-bromomethyl-propionic acid methyl ester (30 g, 115 mmol) was added to a stirred solution of freshly distilled 1-cyclohex-1-enyl-pyrrolidine (20.4 mL, 126 mmol) and triethyl amine (35 mL, 252 mmol) in dry CH$_3$CN (400 mL). After the addition, the mixture was heated (100° C.) and stirred for twelve hours before acetic acid (20 mL) and water (100 mL) were added. Then, heating was continued for another three hours. The solvent was evaporated and the residue was partitioned with diethyl ether and water. The organic phase was washed with a NaHCO$_3$ solution until the washes became basic. It was then dried, filtered, and evaporated. The residue was purified over silica gel using 2-30% diethyl ether in hexanes to give the title compound as a clear oil.

EXAMPLE 7B

9-Amino-bicyclo[3.3.1]nonane-3-carboxylic acid methyl ester

The product of Example 7A (2.03 g, 10.38 mmol) was stirred at room temperature in the presence of ammonium acetate (8 g, 103.8 mmol) and NaBH$_3$CN (3.3 g, 51.9 mmol) in methanol (30 mL) for twelve hours at 23° C. The solvent was then evaporated and the residue was dissolved in dichloromethane; washed with water, NaHCO$_3$ solution, and brine; and dried (Na$_2$SO$_4$). After filtration and evaporation of the solvent, the amine was used without further purification.

EXAMPLE 7C

9-[4-(tert-Butyl-diphenyl-silanyloxymethyl)-3,3-dimethyl-2-oxo-pyrrolidin-1-yl]-bicyclo[3.3.1]nonane-3-carboxylic acid methyl ester The product of Example 7B (0.5 g, 2.34 mmol) and the product of Example 5I (0.8 g, 1.95 mmol) was stirred in the presence of ground 4 Å molecular sieves (1 g) in dry tetrahydrofuran (20 mL) for five hours at 23° C. Sodium triacetoxyborohydride (1.0 g, 4.8 mmol) was added to the mixture and the reaction was stirred at room temperature overnight. The mixture was then filtered through a pad of Celite and concentrated. The residue was dissolved in toluene and heated (100° C.) for three hours before evaporation of solvent. The residue was purified over silica gel using 5-70% ethyl acetate in hexanes to give the title compound.

EXAMPLE 7D 9-(4-Hydroxymethyl-3,3-dimethyl-2-oxo-pyrrolidin-1-yl)-bicyclo[3.3.1]nonane-3-carboxylic acid methyl ester Tetrabutyl ammonium fluoride (3.2 mL, 1 M in tetrahydrofuran, 3.2 mmol) was added to a stirred solution of Example 7C (0.9 g, 1.56 mmol) in tetrahydrofuran at room temperature. The resulting solution was stirred for two hours and then partitioned with ethyl acetate and water. The organic phase was washed with brine, dried (MgSO$_4$), filtered, and evaporated. The residue was purified over silica gel using 20-100% ethyl acetate in hexanes to give the title product as a white solid.

EXAMPLE 7E

9-[4-(5-Cyano-pyridin-2-yloxymethyl)-3,3-dimethyl-2-oxo-pyrrolidin-1-yl]-bicyclo[3.3.1]nonane-3-carboxylic acid methyl ester NaH (0.1 g, 60% in oil, 2.56 mmol) was added in one portion to a stirred and cooled (0° C.) solution of the product of Example 7D (0.48 g, 1.42 mmol) and 6-chloro-nicotinonitrile (0.35 g, 2.56 mmol) in tetrahydrofuran (7 ml) and 1,3-dimethyl-3,4,5,6-tetrahydro-2(1H)-pyrimidinone (7 mL). After the addition, the solution was warmed to room temperature and stirred for another five hours. The dark brown reaction mixture was cooled (0° C.), quenched with acetic acid (0.1 mL), and partitioned with diethyl ether and water. The organic phase was washed with water and brine, dried (MgSO$_4$), filtered, and evaporated. The residue was purified over silica gel using 5-80% ethyl acetate in hexanes to give the titled product as a solid.

EXAMPLE 7F

9-[4-(5-Cyano-pyridin-2-yloxymethyl)-3,3-dimethyl-2-oxo-pyrrolidin-1-yl]-bicyclo[3.3.1]nonane-3-carboxylic acid LiOH (0.2 g, 4.84 mmol) was added in one portion to a stirred solution of the product of Example 7E (0.532 g, 1.21 mmol) in a mixture of tetrahydrofuran (6 mL), methanol (3 mL), and water (3 mL). The resulting solution was stirred overnight, followed by partitioning with diethyl ether and water. The organic layer was washed with water and the combined water layers were acidified with NaHSO$_4$ solution and extracted with ethyl acetate. The combined ethyl acetate phases were dried (MgSO$_4$), filtered, and evaporated. The acid product was used without further purification.

EXAMPLE 7G 9-(4-{[(5-cyanopyridin-2-yl)oxy]methyl}-3,3-dimethyl-2-oxopyrrolidin-1-yl)bicyclo[3.3.1]nonane-3-carboxamide 1-ethyl-3-[3-(dimethylamino)propyl]-carbodiimide hydrochloride (0.35 g, 1.81 mmol) was added in one portion to a stirred solution of the product of Example 7F (0.50 g, 1.21 mmol), 1-hydroxybenzotriazole hydrate (0.32 g, 2.42 mmol), and diisopropylethyl amine (0.63 mL, 3.63 mmol) in dry dichloromethane (7 mL). The resulting solution was stirred at room temperature for two hours before ammonia solution (2.5 mL, 2 M in isopropanol, 4.8 mmol) was added. The resulting white suspension was stirred for one hour before it was diluted with dichloromethane (50 mL) and washed with 20% NaHSO$_4$ solution, 1 M NaOH, water, and brine. The solution was then dried (Na$_2$SO$_4$), filtered, and evaporated. The residue was purified over silica gel using 1-10% methanol in dichloromethane to give the title product as a white solid. $^1$H NMR (300 MHz, CDCl$_3$) δ ppm 1.08 (s, 3H) 1.24 (s, 3H) 1.32-1.51 (m, 2H) 1.50-2.14 (m, 8H) 2.17-2.59 (m, 3H) 2.57-2.75 (m, 1H) 3.27-3.45 (m, 1H) 3.64-3.83 (m, J=9.66, 7.63 Hz, 1H) 3.92 (s, 1H) 4.31-4.45 (m, 1H) 4.46-4.61 (m, 1H) 5.38 (s, 1H) 5.54 (s, 1H) 6.83 (dd, J=8.82, 0.68 Hz, 1H) 7.81 (dd, J=8.82, 2.37 Hz, 1H) 8.48 (dd, J=2.37, 0.68 Hz, 1H).). MS (ESI+) m/z 411.2 (M+H)$^+$.

EXAMPLE 8

Trans ethyl (1R,7S)-4-(4-{[(5-cyanopyridin-2-yl)oxy]methyl}-3,3-dimethyl-2-oxopyrrolidin-1-yl)bicyclo[5.1.0]octane-8-carboxylate and trans ethyl (1S,7R)-4-(4-{[(5-cyanopyridin-2-yl)oxy]methyl}-3,3-dimethyl-2-oxopyrrolidin-1-yl)bicyclo[5.1.0]octane-8-carboxylate

EXAMPLE 8A

Nona-1,8-dien-5-ol

3-Butenyl-magnesium bromide (125 mL, 0.5 M in tetrahydrofuran, 62.5 mmol) was added drop wise to a stirred and cooled (-78° C.) solution of pent-4-enal (4 g, 48.07 mmol) in dry tetrahydrofuran (160 mL). After the addition, the solution was warmed to room temperature and then quenched with NH$_4$Cl solution. The mixture was partitioned with diethyl ether and the organic phase was washed with brine, dried (MgSO$_4$), filtered, and evaporated. The residue was purified over silica gel using 5-15% diethyl ether in hexanes to give the title compound as an oil.

EXAMPLE 8B

Cyclohept-4-enol

RuCl$_2$(Pcy$_3$)$_2$=CHPh (Grubb's I catalyst) (0.93 g, 1.13 mmol) was added in one portion to a degassed solution of the product of Example 8A (3.97 g, 28.33 mmol) in dichloromethane (300 mL). The resulting solution was refluxed for three hours before cooling and concentrated. The residue was purified over silica gel using 2-20% diethyl ether in hexanes to give the title compound as an oil.

EXAMPLE 8C tert-butyl-(cyclohept-4-enyloxy)-diphenyl-silane

A solution of the product of Example 8B (1.57 g, 14.05 mmoles), imidazole (1.43 g, 21.08 mmoles), and Tert-butyl-chlorodiphenylsilane (4.76 gm, 17.4 mmoles) in N,N-dimethylformamide (10 mL) was stirred for five hours at 23° C. The reaction was partitioned between ethyl acetate and water. The organic layer was washed with brine (25 mL), dried with MgSO$_4$, filtered, and solvent evaporated in vacuo. The crude product was purified by flash column chromatography (hexanes:ethyl acetate 100:0 to 90:10) to provide the title compound as an oil.

EXAMPLE 8D 4-(tert-butyl-diphenyl-slianyloxy)-bicyclo[5.1.0]octane-8-carboxylic acid ethyl ester To a solution of Example 8C (2.2 g, 6.28 mmoles) and Rh$_2$(OAc)$_4$ (2 mg, 4.3 µmol) in dichloromethane (2 mL), ethyl diazoacetate (0.717 g, 6.28 mmoles) in dichloromethane (4 mL) was added over two hours via a syringe pump. The solvent was evaporated in vacuo and product purified by flash column chromatography (hexanes:ethyl acetate 100:0 to 80:20) to provide the title compound.

EXAMPLE 8E

4-hydroxy-bicyclo[5.1.0]octane-8-caroxylic acid ethyl ester

A solution of Example 8D (2.2 g, 5.0 mmoles) was taken in ethanol (8 mL) and 12M HCl (1 mL) was added. The reaction was stirred at room temperature for twelve hours. The solvent was evaporated in vacuo and the residue was purified by flash column chromatography (hexanes; ethyl acetate 100:0 to 50:50) to obtain the titled compound as a mixture of diastereomers.

EXAMPLE 8F

Trans ethyl (1R,7S)-4-oxobicyclo[5.1.0]octane-8-carboxylate and trans ethyl (1S,7R)-4-oxobicyclo[5.1.0]octane-8-carboxylate A solution of Example 8E (0.16 g, 0.81 mmoles) was taken in dichloromethane (2.5 mL) and Dess-Martin periodinane (0.37 g, 0.88 mmoles) was added. The resulting solution was stirred at room temperature for two hours. The reaction was quenched with sodium bisulfite and extracted with dichloromethane. The organic phase was washed with 10% $NaHCO_3$ (10 mL) and brine (10 mL), dried with $MgSO_4$, filtered, and evaporated in vacuo. The product was purified by flash column chromatography (hexanes:ethyl acetate 100:0 to 60:40) to provide the title compound as an oil.

EXAMPLE 8G

Trans ethyl (1R,7S)-4-aminobicyclo[5.1.0]octane-8-carboxylate and trans ethyl (1S,7R)-4-aminobicyclo[5.1.0]octane-8-carboxylate A solution of Example 8F (0.135 g, 0.72 mmoles), O-benzyl hydroxylamine hydrochloride (0.12 g, 0.79 mmoles), ammonium acetate (0.138 g, 1.79 mmoles) in EtOH (1.25 mL) was refluxed for 1.5 hours. The solvent was evaporated in vacuo and purified by flash column chromatography (hexanes:ethyl acetate 50:50) to provide the oxime. The oxime was dissolved in ethanol with 7M ammonia (5 mL) and 10% Pd was added on activated carbon (50 mg) and stirred under hydrogen at balloon pressure for twelve hours. The reaction was filtered through celite and evaporated in vacuo to provide the title compound.

EXAMPLE 8H

Trans ethyl (1R,7S)-4-({[tert-butyl(dimethyl)silyl]oxy}methyl)bicyclo[5.1.0]octane-8-carboxylate and trans ethyl (1S,7R)-4-({[tert-butyl(dimethyl)silyl]oxy}methyl)bicyclo[5.1.0]octane-8-carboxylate A solution of Example 8G (94 mg, 0.3 mmoles), Example 2D (75 mg, 0.26 mmoles), and MP-TABH (0.34 g, 0.65 mmoles) in tetrahydrofuran (1.75 mL) was stirred at room temperature for twelve hours. The reaction was filtered and solvent evaporated in vacuo. The residue was taken in toluene (1.5 mL) and heated at 80° C. for three hours. The solvent was evaporated in vacuo to provide the title compound.

EXAMPLE 8I

Trans ethyl (1R,7S)-4-(4-{[(5-cyanopyridin-2-yl)oxy]methyl}-3,3-dimethyl-2-oxopyrrolidin-1-yl)bicyclo[5.1.0]octane-8-carboxylate and trans ethyl (1S,7R)-4-(4-{[(5-cyanopyridin-2-yl)oxy]methyl}-3,3-dimethyl-2-oxoppyrrolidin-1-yl)bicyclo[5.1.0]octane-8-carboxylate A solution of Example 8H (55 mg, 0.12 mmoles) was dissolved in ethanol (1.25 mL) and two drops of 12M HCl was added. The reaction was stirred for two hours at room temperature. The solvent was evaporated in vacuo. The residue was taken in N,N-dimethylformamide (1.25 mL) and NaH (10 mg, 0.25 mmoles) and 6-chloronicotinonitrile (24 mg, 0.18 mmoles) were added and stirred for one hour. The reaction was quenched with 10 $NH_4Cl$ and the product was extracted with ethyl acetate. The organic phase was evaporated in vacuo and the crude reaction mixture was purified by preparative reverse phase HPLC on a Waters Symmetry C8 column (25 mm×100 mm, 7 um particle size) using a gradient of 20% to 100% acetonitrile:water (0.1% trifluoroacetic acid) over eighteen minutes at a flow rate of 40 mL/minute to provide the title compound as the trifluoroacetic acid salt. $^1$H NMR (300 MHz, $CDCl_3$) δ ppm 8.48 (dd, J=2.33, 0.64 Hz, 1H), 7.80 (dd, J=8.66, 2.33 Hz, 1H), 6.82 (dd, J=8.66, 0.78 Hz, 1H), 4.49 (dd, J=10.87, 6.04 Hz, 1H), 4.11 (m, 2H), 4.03-4.19 (m, 1H), 3.96 (dd, J=10.86, 8.24 Hz, 1H), 3.46 (dd, J=9.85, 7.64 Hz, 1H), 3.08 (dd, J=9.87, 7.94 Hz, 1H), 2.45 (qd, J=7.94, 6.01 Hz, 1H), 2.21 (m, 1H), 1.43-1.82 (m, 10H), 1.24 (m, 6H), 1.06 (m, 3H). MS ($APCI^+$) m/z 426.48 $(M+H)^+$.

EXAMPLE 9

6-{[4,4-dimethyl-1-(4-methylbicyclo[2.2.2]oct-1-yl)-5-oxopyrrolidin-3-yl]methoxy}nicotinonitrile

EXAMPLE 9A

4-(tert-butyl-dimethyl-silanyloxymethyl)-3,3-dimethyl-1-(4-methyl-bicyclo[2.2.2]oct-1-yl)-pyrrolidin-2-one A solution of 4-methyl-bicyclo[2.2.2]oct-1-ylamine (43 mg, 0.32 mmoles), Example 2D (75 mg, 0.26 mmoles), and MP-triacetoxyborohydride (0.22 g, 0.52 mmoles) in tetrahydrofuran (1.75 mL) was stirred for twelve hours at 23° C. The reaction was filtered and solvent evaporated in vacuo. The residue was taken in toluene (1.5 mL) and heated to 80° C. for three hours. The solvent was evaporated in vacuo to provide the title compound.

EXAMPLE 9B 6-{[4,4-dimethyl-1-(4-methylbicyclo[2.2.2]oct-1-yl)-5-oxopyrrolidin-3-yl]methoxy}nicotinonitrile A solution of Example 9A (60 mg, 0.16 mmoles) was dissolved in methanol and two drops of concentrated HCl were added. The resulting solution was stirred at room temperature for one hour. The solvent was evaporated in vacuo and the residue taken in N,N-dimethylformamide (1.5 mL) and 60% NaH (10 mg, 0.24 mmoles) and 6 chloronicotinonitrile (27 mg, 0.2 mmoles) were added and stirred for one hour. The reaction was quenched with 10% $NH_4Cl$ and extracted with ethyl acetate. The organic layer was separated and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% trifluoroacetic acid) over eighteen minutes at a flow rate of 40 mL/minute to provide the title compound as the trifluoroacetic acid salt. $^1$H NMR (500 MHz, CDCl$_3$) δ ppm 8.47 (dd, J=2.36, 0.69 Hz, 1H), 7.79 (dd, J=8.70, 2.29 Hz, 1H), 6.80 (dd, J=8.70, 0.76 Hz, 1H), 4.46 (dd, J=10.83, 5.95 Hz, 1H), 4.32 (dd, J=10.83, 8.24 Hz, 1H), 3.53 (dd, J=9.99, 7.55 Hz, 1H), 3.11 (dd, J=9.84, 8.16 Hz, 1H), 2.38 (qd, J=7.97, 6.25 Hz, 1H), 1.92-2.05 (m, 6H), 1.47 (t, J=8.01 Hz, 6H), 1.18 (s, 3H), 1.01 (s, 3H), 0.78 (s, 3H). MS (APCI+) m/z 368.2. (M+H)$^+$.

EXAMPLE 10

6-{[1-(5-cyanocyclooctyl)-4,4-dimethyl-5-oxopyrrolidin-3-yl]methoxy}nicotinonitrile

EXAMPLE 10A 5-(tert-Butyl-dimethyl-silanyloxy)-cyclooctanecarbonitrile

Potassium tert-butoxide (30.4 mL, 1 M in tetrahydrofuran, 30.4 mmol) was added drop wise to a stirred and cooled (0° C.) solution of tosylmethyl isocyanide (4.74 g, 24.27 mmol) in dry DME (40 mL). After ten minutes, dry methanol (0.98 mL, 24.28 mmol) was added and followed by a solution of the product of Example 5B (3.11 g, 12.14 mmol) in DME (10 mL). The resulting solution was allowed to warm to room temperature and then heated (45° C.) for thirty minutes. After cooling, the reaction mixture was partitioned with diethyl ether and water. The organic phase was washed with brine, dried (MgSO$_4$), filtered, and evaporated. The residue was purified over silica gel using 2-10% diethyl ether in hexanes to give the title compound as an oil.

EXAMPLE 10B

5-Oxo-cyclooctanecarbonitrile

Tetrabutyl ammonium fluoride (3.9 mL, 1 M in tetrahydrofuran, 3.89 mmol) was added to a stirred solution of Example 10A (0.52 g, 1.95 mmol) in tetrahydrofuran (10 mL) at room temperature. The resulting solution was stirred for two hours and then partitioned with diethyl ether and water. The organic phase was washed with brine and dried (MgSO$_4$), filtered, and evaporated. The residue was purified over silica gel using 2-30% diethyl ether in hexanes to give the corresponding alcohol product as an oil. Tetrapropylammonium perruthenate (33 mg, 0.096 mmol) was added to a stirred and cooled (0° C.) solution of the residue (0.294 g, 1.920 mmol), N-methylmorpholine N-oxide (0.33 g, 2.85 mmol), and 4 Å molecular sieves (1 g) in dry dichloromethane (10 mL). After the addition, the mixture was warmed to room temperature and stirred for another three hours. The black mixture was filtered through a pad of Celite and the solvent was evaporated. The residue was purified over silica gel using 5-15% ethyl acetate in hexanes to give the title compound as an oil.

EXAMPLE 10C

5-Amino-cyclooctanecarbonitrile

The product of Example 10B (0.259 g, 1.71 mmol), ammonium acetate (1.32 g, 17.14 mmol), and sodium cyanoborohydride (0.43 g, 6.84 mmol) was stirred in methanol (8 mL) for twelve hours. The solvent was evaporated and the residue was partitioned with dichloromethane and water. The organic phase was washed with NaHCO$_3$ solution and brine, dried (Na$_2$SO$_4$), filtered, and evaporated. The crude title compound was used in the following step without further purification.

EXAMPLE 10D

5-[4-(tert-butyl-dimethyl-silanyloxymethyl)-3,3-dimethyl-2-oxo-pyrrolidin-1-yl]-cyclooctanecarbonitrile A solution of the product of Example 10C (47 mg, 0.31 mmoles), Example 2D (75 mg, 0.26 mmoles), and MP-triacetoxyborohydride (0.22 g, 0.52 mmoles) in tetrahydrofuran (1.75 mL) was stirred for twelve hours at room temperature. The reaction was filtered and solvent evaporated in vacuo. The residue was taken in toluene (1.5 mL) and heated at 80° C. for three hours. The solvent was evaporated in vacuo to provide the title compound.

EXAMPLE 10E

6-{[1-(5-cyanocyclooctyl)-4,4-dimethyl-5-oxopyrrolidin-3-yl]methoxy}nicotinonitrile To a solution of Example 10D (65 mg, 0.16 mmoles) in methanol, one drop of 6 M HCl was added. The resulting solution was stirred for two hours at room temperature. The solvent was evaporated in vacuo. The residue was taken in N,N-dimethylformamide (1.5 mL) and 60% NaH (10 mg, 0.24 mmoles) and 6-chloronicotinonitrile (26 mg, 0.19 mmoles) were added and stirred for one hour at room temperature. The reaction was quenched with 10% NH$_4$Cl and extracted with ethyl acetate. The organic layer was separated and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% trifluoroacetic acid) over eighteen minutes at a flow rate of 40 mL/minute to provide the title compound as the trifluoroacetic acid salt. $^1$H NMR (300 MHz, CDCl$_3$) δ ppm 8.48 (dd, J=2.33, 0.64 Hz, 1H), 7.80 (dd, J=8.66, 2.33 Hz, 1H), 6.82 (dd, J=8.66, 0.78 Hz, 1H), 4.50 (dd, J=10.87, 6.04 Hz, 1H), 4.36 (dd, J=10.86, 8.24 Hz, 1H), 4.03-4.19 (m, 1H), 3.46 (dd, J=9.85, 7.64 Hz, 1H), 3.08 (dd, J=9.87, 7.94 Hz, 1H), 2.80 (m, 1H), 2.45 (qd, J=7.94, 6.01 Hz, 1H), 1.43-1.82 (m, 12H), 1.24 (s, 3H), 1.06 (s, 3H). MS (APCI$^+$) m/z 381.3 (M+H)$^+$.

EXAMPLE 11

E-4-(4-{[(5-cyanopyridin-2-yl)oxy]methyl}-3,3-dimethyl-2-oxopyrrolidin-1-yl)adamantane-1-carbonitrile

EXAMPLE 11A

E-4-(carbamic acid benzyl ester)-adamantane-1-carboxamide

Step A

Benzyl chloroformate (3.48 mL, 24.72 mmol) was added drop wise to a stirred and cooled (0C) solution of Example 6B (5.05 g, 20.60 mmol) and diisopropylethylamine (7.9 mL, 45.32 mmol) in dry dichloromethane (100 mL). After the addition, the solution was allowed to warm to room temperature and was stirred for another two hours. Saturated NaHCO$_3$ solution was added to quench the reaction and the phases were separated. The organic phase was washed with NaHSO$_4$ solution and NaHCO$_3$ solution; dried (Na$_2$SO$_4$); and concentrated. The residue was purified over silica gel using 20% ethyl acetate in hexanes and concentrated.

Step B

The product from step A (6.49 g, 18.91 mmol) was dissolved in dry tetrahydrofuran (90 mL) and potassium trimethylsilanolate (4.85 g, 37.82 mmol) was added at room temperature. The resulting solution was stirred overnight before water (100 mL) and diethyl ether (100 mL) were added and the phases were separated. The aqueous phase was acidified using solid NaHSO$_4$ until a pH of 1 was reached. The aqueous phase was then extracted using ethyl acetate. The combined organic extract was dried (MgSO$_4$) and concentrated.

Step C

The product from step C (18.91 mmol) was dissolved in dry dichloromethane (60 mL) and diisopropylethylamine (10 mL, 56.7 mmol). 1-hydroxybenzotriazole hydrate (5.1 g, 37.82 mmol) and 1-ethyl-3-[3-(dimethylamino)propyl]-carbodiimide hydrochloride (5.4 g, 28.36 mmol) were added to the solution. The resulting mixture was stirred for one hour at room temperature before NH$_3$ (30 mL, 2 M in isopropanol, 56.7 mmol) was added. After one hour, the solution was diluted with dichloromethane (200 mL) and washed with NaHSO$_4$ solution, 1 M NaOH, and water. Then the solution was dried (Na$_2$SO$_4$). The residue was purified over silica gel using 5% methanol in dichloromethane to provide the title compound as a solid.

EXAMPLE 11B

E-4-Amino-adamantane-1-carbonitrile

The product of Example 11A (18.91 mmol) was dissolved in dry dichloromethane (60 mL) and triethyl amine (10.5 mL, 75.64 mmol). Trifluoroacetic acid anhydride (7.9 mL, 56.73 mmol) was added drop wise to the solution at 0° C. After the addition, the solution was allowed to warm to room temperature and stirred for three hours before methanol was added to quench the reaction. The solution was washed with NaHSO$_4$ solution, NaHCO$_3$ solution, and dried (Na$_2$SO$_4$). The residue was purified over silica gel using 30% ethyl acetate and concentrated. Pd(OH)$_2$/C (0.9 g) was added to a solution of the above nitrile (3.22 g, 10.38 mmol) in methanol (15 mL). The solution was stirred at room temperature under H$_2$ (balloon) until the starting material was consumed. The mixture was filtered through a pad of Celite and concentrated in vacuo to provide the title compound as a solid.

EXAMPLE 11C

E-4-[4-(tert-Butyl-diphenyl-silanyloxymethyl)-3,3-dimethyl-2-oxo-pyrrolidin-1-yl]-adamantane-1-carbonitrile The product of Example 11B (0.29 g, 1.64 mmol), the product of Example 5I (0.72 g, 1.49 mmol), and ground 4 Å molecular sieves (1 g) in dry tetrahydrofuran (15 mL) were stirred at room temperature for five hours. Sodium triacetoxyborohydride (0.8 g, 3.72 mmol) was added to the mixture and the reaction was allowed to stir at room temperature overnight. The resulting thick white suspension was filtered through a pad of Celite and the solvent was evaporated. The residue was redisolved in toluene (10 mL) and heated to 100° C. for two hours. The solvent was then evaporated and the residue was purified over silica gel using 10-50% ethyl acetate in hexanes to give the titled product as a thick oil.

EXAMPLE 11D

E-4-(4-Hydroxymethyl-3,3-dimethyl-2-oxo-pyrrolidin-1-yl)-adamantane-1-carbonitrile Tetrabutyl ammonium fluoride (1.64 mL, 1 M in tetrahydrofuran, 1.64 mmol) was added to a stirred solution of the product of Example 11C (0.74 g, 1.36 mmol) in tetrahydrofuran (5 mL) at room temperature. The resulting solution was stirred for two hours at 23° C. and then partitioned with ethyl acetate and water. The organic phase was washed with brine and dried (MgSO$_4$), filtered, and evaporated. The residue was purified over silica gel using 20-100% ethyl acetate in hexanes to give the titled product as a white solid.

EXAMPLE 11E

E-4-(4-{[(5-cyanopyridin-2-yl)oxy]methyl}-3,3-dimethyl-2-oxopyrrolidin-1-yl)adamantane-1-carbonitrile NaH (0.4 g, 60% in oil, 0.99 mmol) was added in one portion to a stirred and cooled (0° C.) solution of the product of Example 11D (0.15 g, 0.496 mmol), 6-chloro-nicotinonitrile (0.18 g, 0.992 mmol) in tetrahydrofuran (2 ml), and 1,3-dimethyl-3,4,5,6-tetrahydro-2(1H)-pyrimidinone (2 mL). After the addition, the solution was warmed to room temperature and stirred for another twelve hours. The dark brown reaction mixture was cooled (0° C.) and quenched with acetic acid (0.1 mL) and partitioned with diethyl ether and water. The organic phase was washed with water and brine, dried (MgSO$_4$), filtered, and evaporated. The residue was purified over silica gel using 5-80% ethyl acetate in hexanes to give the title compound as a solid. $^1$H NMR (300 MHz, CDCl$_3$) δ ppm 8.48 (dd, J=2.37, 0.76 Hz, 1H), 7.80 (dd, J=8.69, 2.33 Hz, 1H), 6.82 (dd, J=8.73, 0.76 Hz, 1H), 4.52 (dd, J=10.94, 5.93 Hz, 1H), 4.38 (dd, J=10.94, 8.14 Hz, 1H), 3.89-3.92 (m, 1H), 3.71 (dd, J=9.58, 7.63 Hz, 1H), 3.32 (dd, J=9.58, 8.05 Hz, 1H), 2.50 (qd, J=8.00, 6.13 Hz, 1H), 2.44-2.48 (m, 2H), 2.17-2.24 (m, 2H), 2.10-2.17 (m, 2H), 2.04-2.10 (m, 3H), 1.90-1.99 (m, 1H), 1.82-1.90 (m, 1H), 1.62-1.71 (m, 2H), 1.24 (s, 3H), 1.08 (s, 3H). MS (ESI+) m/z 405.2 (M+H)$^+$.

EXAMPLE 12

E-4-(3,3-dimethyl-2-oxo-4-{[4-(1H-1,2,4-triazol-1-yl)phenoxy]methyl}pyrrolidin-1-yl)adamantane-1-carboxamide

EXAMPLE 12A

E-4-[3,3-Dimethyl-2-oxo-4-(4-[12,4]triazol-1-yl-phenoxymethyl)-pyrrolidin-1-yl]-adamantane-1-carboxylic acid methyl ester The product of Example 6D (50 mg, 0.149 mmol), 4-[1,2,4]triazol-1-yl-phenol (36 mg, 0.223 mmol), di-tert-butyl azodicarboxylate (60 mg, 0.298 mmol), triphenylphosine polymer-supported (0.25 g, 3 mmol/g, 0.745 mmol) in dry tetrahydrofuran (3 mL) were sealed in a tube and heated (80° C.) for ten hours. After cooling and filtration, the solvent was evaporated and the residue was treated with trifluoroacetic acid (2 mL) for thirty minutes. Trifluoroacetic acid was evaporated and the residue was purified on HPLC using $CH_3CN$/water 1% trifluoroacetic acid as an eluent to provide the title compound as an oil.

EXAMPLE 12B

E-4-(3,3-dimethyl-2-oxo-4-{[4-(1H-1,2,4-triazol-1-yl)phenoxy]methyl}pyrrolidin-1-yl)adamantane-1-carboxamide Potassium trimethylsilanolate (20 mg, 0.164 mmol) was added to a stirred solution of the product of Example 12A (4.1 mg, 0.008 mmol) in tetrahydrofuran (2 mL). After five hours, trifluoroacetic acid (1 mL) was added and the volatiles were evaporated. O-(7-azabenzotriazol-1-yl)-N,N,N',N'-tetramethyluronium hexafluorophosphate (51 mg, 0.135 mmol) and diisopropylethylamine (0.1 mL) were added to the crude acid and stirred for thirty minutes before the addition of an ammonia solution (2 mL, 2 M in isopropyl alcohol). After one hour, the volatiles were evaporated and the residue was purified on HPLC using $CH_3CN$/water 1% trifluoroacetic acid as eluent to provide the trifluoroacetic acid salt of the title compound as an oil. $^1$H NMR (300 MHz, $CD_3OD$) δ ppm 8.98 (s, 1H), 8.15 (s, 1H), 7.68-7.75 (m, 2H), 7.10-7.15 (m, 2H), 4.22 (dd, J=9.58, 6.19 Hz, 1H), 4.14 (dd, J=9.54, 6.74 Hz, 1H), 3.88-3.95 (m, 2H), 3.51-3.58 (m, 1H), 2.53-2.61 (m, 1H), 2.37-2.43 (m, 2H), 1.86-2.11 (m, 8H), 1.62-1.72 (m, 2H), 1.26 (s, 3H), 1.10 (s, 3H). MS (ESI+) m/z 464.3 (M+H)$^+$.

EXAMPLE 13

E-4-(4-{[4-(1H-imidazol-1-yl)phenoxy]methyl}-3,3-dimethyl-2-oxopyrrolidin-1-yl)adamantane-1-carboxamide

EXAMPLE 13A

E-4-[4-(4-Imidazol-1-yl-phenoxymethyl)-3,3-dimethyl-2-oxo-pyrrolidin-1-yl]-adamantane-1-carboxylic acid methyl ester The product of Example 6D (50 mg, 0.149 mmol), 4-imidazol-1-yl-phenol (36 mg, 0.223 mmol), di-tert-butyl azodicarboxylate (60 mg, 0.298 mmol), and triphenylphosphine, polymer-supported (0.25 g, 3 mmol/g, 0.745 mmol) in dry tetrahydrofuran (3 mL) were sealed in a tube and heated (80° C.) for ten hours. After cooling and filtration, the solvent was evaporated and the residue was treated with trifluoroacetic acid (2 mL) for thirty minutes. Trifluoroacetic acid was evaporated and the residue purified on HPLC using $CH_3CN$/water 1% trifluoroacetic acid as eluent to provide the title compound as an oil.

EXAMPLE 13B

E-4-(4-{[4-(1H-imidazol-1-yl)phenoxy]methyl}-3,3-dimethyl-2-oxopyrrolidin-1-yl)adamantane-1-carboxamide Potassium trimethylsilanolate (20 mg, 0.164 mmol) was added to a stirred solution of the product of Example 13A (13.1 mg, 0.027 mmol) in tetrahydrofuran (2 mL). After five hours, trifluoroacetic acid (1 mL) was added and the volatiles were evaporated. O-(7-azabenzotriazol-1-yl)-N,N,N',N'-tetramethyluronium hexafluorophosphate (51 mg, 0.135 mmol) and diisopropylethyl amine (0.1 mL) were added to the crude acid and stirred for thirty minutes before the addition of ammonia solution (2 mL, 2 M in isopropanol). After one hour, the volatiles were evaporated and the residue was purified on HPLC using $CH_3CN$/water 1% trifluoroacetic acid as eluent to provide the trifluoroacetic acid salt of the title compound as an oil. $^1$H NMR (300 MHz, $CD_3OD$) δ ppm 9.36 (t, J=1.44 Hz, 1H), 7.99 (t, J=1.78 Hz, 1H), 7.74 (dd, J=1.99, 1.48 Hz, 1H), 7.61-7.68 (m, 2H), 7.16-7.23 (m, 2H), 4.24 (dd, J=9.75, 6.27 Hz, 1H), 4.17 (dd, J=9.58, 6.61 Hz, 1H), 3.89-3.96 (m, 2H), 3.55 (dd, J=9.87, 7.42 Hz, 1H), 2.58 (qd, J=7.15, 6.61 Hz, 1H), 2.37-2.44 (m, 2H), 1.89-2.09 (m, 9H), 1.62-1.73 (m, 2H), 1.26 (s, 3H), 1.10 (s, 3H). MS (ESI+) m/z 463.3 (M+H)+

EXAMPLE 14

E-4-[3,3-dimethyl-2-oxo-4-({[5-(trifluoromethyl)pyridin-2-yl]oxy}methyl)pyrrolidin-1-yl]-N'-hydroxyadamantane-1-carboximidamide

EXAMPLE 14A

E-4-[3,3-Dimethyl-2-oxo-4-(5-trifluoromethyl-pyridin-2-yloxymethyl)-pyrrolidin-1-yl]-adamantane-1-carbonitrile NaH (0.4 g, 60% in oil, 0.99 mmol) was added in one portion to a stirred and cooled (0° C.) solution of the product of Example 11D (0.15 g, 0.496 mmol), 2-chloro-5-trifluoromethyl-pyridine (0.18 g, 0.992 mmol) in tetrahydrofuran (2 ml), and 1,3-dimethyl-3,4,5,6-tetrahydro-2(1H)-pyrimidinone (2 mL). After the addition, the solution was warmed to room temperature and stirred for another twelve hours. The dark brown reaction mixture was cooled (0° C.) and quenched with acetic acid (0.1 mL) and partitioned with diethyl ether and water. The organic phase was washed with water and brine, dried ($MgSO_4$), filtered, and evaporated. The residue was purified over silica gel using 5-80% ethyl acetate in hexanes to give the title compound as a solid.

EXAMPLE 14B

E-4-[3,3-dimethyl-2-oxo-4-({[5-(trifluoromethyl)pyridin-2-yl]oxy}methyl)pyrrolidin-1-yl]-N'-hydroxyadamantane-1-carboximidamide The product of Example 14A (0.209 g, 0.479 mmol), hydroxylamine hydrochloride (0.13 g, 1.86 mmol), and diisopropylethyl amine (0.65 mL, 3.7 mmol) in dry dimethylsulfoxide (4 mL) were heated (100° C.) for twelve hours before it was diluted with ethyl acetate and washed with $NH_4Cl$ solution and brine, dried ($MgSO_4$), and filtered. After evaporation of solvent, the residue was purified on HPLC using $CH_3CN$/water 1% trifluoroacetic acid as eluent to provide the trifluoroacetic acid salt of the title compound as an oil. $^1$H NMR (300 MHz, $CD_3OD$) δ ppm 8.48 (dqd, J=2.60, 1.12, 0.60 Hz, 1H), 7.95 (ddq, J=8.78, 2.59, 0.55 Hz, 1H), 6.94 (dqd, J=8.77, 0.74, 0.64 Hz, 1H), 4.57 (dd, J=10.98, 6.36 Hz, 1H), 4.48 (dd, J=11.00, 7.27 Hz, 1H), 3.90-3.93 (m, 1H), 3.88 (dd, J=9.83, 7.76 Hz, 1H), 3.52 (dd, J=9.83, 7.80 Hz, 1H), 2.59 (qd, J=7.53, 6.50 Hz, 1H), 2.43-2.51 (m, 2H), 1.94-2.17 (m, 9H), 1.65-1.75 (m, 2H), 1.24 (s, 3H), 1.10 (s, 3H). MS (ESI+) m/z 481.2 (M+H)$^+$.

EXAMPLE 15

E-4-[3,3-dimethyl-2-oxo-4-({[5-(trifluoromethyl)pyridin-2-yl]oxy}methyl)pyrrolidin-1-yl]adamantane-1-carboxamide The trifluoroacetic acid salt of the title compound was produced as a minor by-product during the synthesis of Example 14B and was isolated from the purification procedure. $^1$H NMR (300 MHz, CD$_3$OD) δ ppm 8.46-8.49 (m, 1H), 7.92-7.97 (m, 1H), 6.92-6.97 (m, 1H), 4.57 (dd, J=10.96, 6.29 Hz, 1H), 4.47 (dd, J=11.00, 7.27 Hz, 1H), 3.89-3.91 (m, 1H), 3.88 (dd, J=9.90, 7.65 Hz, 1H), 3.52 (dd, J=9.94, 7.69 Hz, 1H), 2.57 (qd, J=7.58, 6.39 Hz, 1H), 2.34-2.41 (m, 2H), 1.88-2.09 (m, 9H), 1.61-1.71 (m, 2H), 1.23 (s, 3H), 1.09 (s, 3H). MS (ESI+) m/z 466.2 (M+H)$^+$.

EXAMPLE 16

E-4-[3,3-dimethyl-2-oxo-4-({[5-(trifluoromethyl)pyridin-2-yl]oxy}methyl)pyrrolidin-1-yl]adamantane-1-carboximidamide A solution of MeAlClNH$_2$ (0.73 mL, 0.67 M, 0.49 mmol) was added to the product of Example 11E (44 mg, 0.098 mmol) in dry toluene (1 mL) at room temperature. The resulting mixture was heated overnight at 90° C. The mixture was cooled to room temperature and NaOH (1 mL, 1 M) was added to quench the reaction. The mixture was partitioned with dichloromethane and water and the water layer was extracted with dichloromethane. The combined organic phases were dried (Na$_2$SO$_4$), filtered, and evaporated. The residue was purified on HPLC using CH$_3$CN/water 1% trifluoroacetic acid as eluent to provide the trifluoroacetic acid salt of the title compound as an oil. $^1$H NMR (300 MHz, CD$_3$OD) δ ppm 8.46-8.49 (m, 1H), 7.92-7.97 (m, 1H), 6.93-6.97 (m, 1H), 4.57 (dd, J=10.94, 6.36 Hz, 1H), 4.48 (dd, J=11.02, 7.29 Hz, 1H), 3.91-3.94 (m, 1H), 3.88 (dd, J=9.88, 7.84 Hz, 1H), 3.52 (dd, J=9.83, 7.71 Hz, 1H), 2.59 (qd, J=7.60, 6.43 Hz, 1H), 2.43-2.52 (m, 2H), 1.95-2.18 (m, 9H), 1.65-1.76 (m, 2H), 1.24 (s, 3H), 1.10 (s, 3H) MS (ESI+) m/z 465.2 (M+H)$^+$.

EXAMPLE 17

E-4-[3,3-Dimethyl-2-oxo-4-(5-trifluoromethyl-pyridin-2-yloxymethyl)-pyrrolidin-1-yl]-adamantane-1-1H-tetrazol-5-yl NaN$_3$ (14 mg, 0.214 mmol) and ZnBr$_2$ (48 mg, 0.214 mmol) were added to the product of Example 14A (48 mg, 0.107 mmol) in water (1 mL) and isopropyl alcohol (0.2 mL) in a pressure tube. The tube was sealed and heated (150° C.) for forty-eight hours. After cooling, the resulting mixture was diluted with ethyl acetate and filtered. The solvent was evaporated and the residue was purified on HPLC using CH$_3$CN/water 1% trifluoroacetic acid as eluent to provide the trifluoroacetic acid salt of the title compound as an oil. $^1$H NMR (300 MHz, CD$_3$OD) δ ppm 1.11 (s, 3H) 1.25 (s, 3H) 1.68-1.82 (m, 1H) 1.82-1.93 (m, 1H) 1.94-2.30 (m, 9H) 2.48 (s, 2H) 2.53-2.70 (m, 1H) 3.55 (dd, J=9.83, 7.80 Hz, 1H) 3.91 (dd, J=10.00, 7.63 Hz, 1H) 4.00 (s, 1H) 4.41-4.53 (m, 1H) 4.54-4.66 (m, 1H) 6.95 (d, J=9.49 Hz, 1H) 7.95 (dd, J=8.98, 2.88 Hz, 1H) 8.48 (d, J=2.71 Hz, 1H). MS (ESI+) m/z 491.3 (M+H)$^+$.

It is understood that the foregoing detailed description and accompanying examples are merely illustrative and are not to be taken as limitations upon the scope of the invention, which is defined solely by the appended claims and their equivalents. Various changes and modifications including, but not limited to, those relating to the chemical structures, substituents, derivatives, intermediates, syntheses, formulations and/or methods of use of the invention, can be made without departing from the spirit and scope thereof.

We claim:
1. A compound of formula (I)

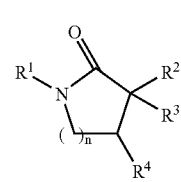

wherein:
n is 1;
R$^1$ is

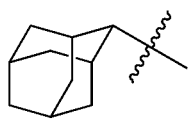
(i)

(ii)

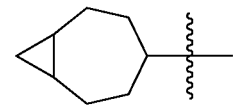
(iii)

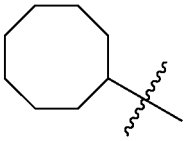
(iv)

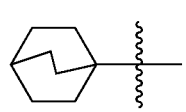
(v)

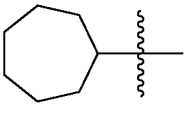
(vi)

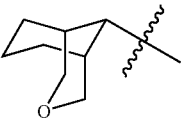
(vii)

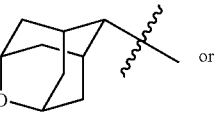
(viii)

 or

-continued

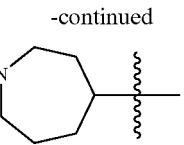
(ix)

each of which is independently unsubstituted or substituted with 1 or 2 substituents independently selected from the group consisting of alkyl, alkenyl, haloalkyl, Cl, Br, F, I, —CN, —NO$_2$, —OR$_b$, —SR$_b$, —S(O)R$_Z$, —S(O)$_2$R$_Z$, —NR$_a$R$_b$, —C(O)R$_b$, —C(O)OR$_b$, —C(O)NR$_a$R$_b$, —S(O)$_2$ NR$_a$R$_b$, —C(=NOH)NH$_2$, —C(=NH)NH$_2$, —R$_c$, —(CR$_d$R$_c$)$_m$—CN, —(CR$_d$R$_c$)$_m$—OR$_b$, —(CR$_d$R$_c$)$_m$—SR$_b$, —(CR$_d$R$_c$)$_m$—S(O)$_2$R$_Z$, —(CR$_d$R$_c$)$_m$—NR$_a$R$_b$, —(CR$_d$R$_c$)$_m$—C(O)R$_b$, —(CR$_d$R$_c$)$_m$—C(O)OR$_b$, —(CR$_d$R$_c$)$_m$—S(O)$_2$NR$_a$R$_b$, —(CR$_d$R$_c$)$_m$—R$_c$, —N(R$_a$)—(CR$_d$R$_c$)$_m$—C(O)OR$_b$, —N(R$_a$)—(CR$_d$R$_c$)$_m$—C(O)OR$_b$, —N(R$_a$)—(CR$_d$R$_c$)$_m$—C(O)NR$_a$R$_b$, —O—(CR$_d$R$_c$)$_m$—C(O)R$_b$, —O—(CR$_d$R$_c$)$_m$—C(O)OR$_b$, and —O—(CR$_d$R$_c$)$_m$—C(O)NR$_a$R$_b$;

R$^2$ and R$^3$, at each occurrence, are each independently hydrogen or alkyl;

R$^4$ is —(CR$_d$R$_c$)$_m$-E-G, wherein E, at each occurrence, is independently O or N(R$_c$), and G, at each occurrence, is independently phenyl or pyridinyl, wherein each G is independently unsubstituted or substituted with 1 or 2 substituents independently selected from the group consisting of alkyl, alkenyl, haloalkyl, Cl, Br, F, I, —CN, —NO$_2$, —OR$_d$, —S(R$_d$), —S(O)(alkyl), —S(O)(haloalkyl), —S(O)$_2$(alkyl), —S(O)$_2$(haloalkyl), —NR$_d$R$_c$, —C(O)(R$_d$), —C(O)OR$_d$, —C(O)NR$_d$R$_c$, —S(O)$_2$NR$_d$R$_c$, —R$_c$, —(CR$_d$R$_c$)$_m$—CN, —(CR$_d$R$_c$)$_m$—NO$_2$, —(CR$_d$R$_c$)$_m$—OR$_d$, —(CR$_d$R$_c$)$_m$—S(R$_d$), —(CR$_d$R$_c$)$_m$—S(O)(alkyl), —(CR$_d$R$_c$)$_m$—S(O)(haloalkyl), —(CR$_d$R$_c$)$_m$—S(O)$_2$(alkyl), —(CR$_d$R$_c$)$_m$—S(O)$_2$(haloalkyl), —(CR$_d$R$_c$)$_m$—NR$_d$R$_c$, —(CR$_d$R$_c$)$_m$—C(O)(R$_d$), —(CR$_d$R$_c$)$_m$—C(O)OR$_d$, —(CR$_d$R$_c$)$_m$—C(O)NR$_d$R$_c$, —(CR$_d$R$_c$)$_m$—S(O)$_2$NR$_d$R$_c$, and —(CR$_d$R$_c$)$_m$—R$_c$;

R$_a$, at each occurrence, is independently hydrogen or alkyl;
R$_b$, at each occurrence, is independently hydrogen, alkyl, haloalkyl, R$_c$ or —(CR$_d$R$_c$)$_m$—R$_c$;
R$_Z$, at each occurrence, is independently alkyl, haloalkyl, R$_c$ or —(CR$_d$R$_c$)$_m$—R$_c$;
R$_c$, at each occurrence, is heteroaryl wherein heteroaryl is imidiazolyl, triazolyl and tetrazolyl, wherein each R$_c$ is independently unsubstituted or substituted with 1 or 2 substituents independently selected from the group consisting of alkyl, alkenyl, haloalkyl, Cl, Br, F, I, —CN, —NO$_2$, —OR$_d$, —S(R$_d$), —S(O)(alkyl), —S(O)(haloalkyl), —S(O)$_2$(alkyl), —S(O)$_2$(haloalkyl), —NR$_d$R$_c$, —C(O)(R$_d$), —C(O)OR$_d$, —C(O)NR$_d$R$_c$, —S(O)$_2$NR$_d$R$_c$, —(CR$_d$R$_c$)$_m$—CN, —(CR$_d$R$_c$)$_m$—NO$_2$, —(CR$_d$R$_c$)$_m$—OR$_d$, —(CR$_d$R$_c$)$_m$—S(R$_d$), —(CR$_d$R$_c$)$_m$—S(O)(alkyl), —(CR$_d$R$_c$)$_m$—S(O)(haloalkyl), —(CR$_d$ R$_c$)$_m$—S(O)$_2$(alkyl), —CR$_d$R$_c$)$_m$—S(O)$_2$(haloalkyl), —(CR$_d$R$_c$)$_m$—NR$_d$R$_c$, —(CR$_d$R$_c$)$_m$—C(O)(R$_d$), —(CR$_d$R$_c$)$_m$—C(O)OR$_d$, —(CR$_d$R$_c$)$_m$—C(O)NR$_d$R$_c$, and —(CR$_d$R$_c$)$_m$—S(O)$_2$NR$_d$R$_c$;
R$_d$ and R$_c$, at each occurrence, are independently hydrogen or alkyl; and
m is 1;
or a pharmaceutically acceptable salt thereof, or a combination thereof.

2. The compound of claim 1, wherein R$^4$ is —CH$_2$—O-G or —CH$_2$—N(R$_c$)-G, and R$^2$ and R$^3$ are C$_{1-6}$ alkyl.

3. The compound of claim 1, wherein R$^1$ is independently unsubstituted or substituted

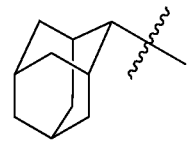
(i)

(ii)

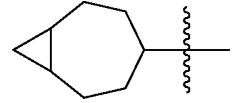
(iii)

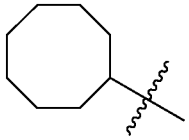
(iv)

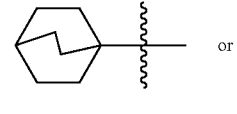
or
(v)

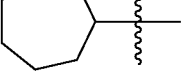
;
(vi)

R$_c$ is hydrogen or methyl, and R$^2$ and R$^3$ are methyl.

4. The compound of claim 1, wherein R$^1$ is

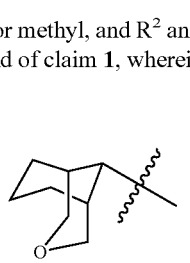
(vii)

(viii)

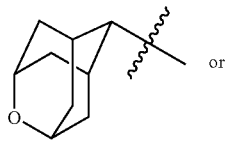
or

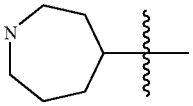
;
(ix)

R$_c$ is hydrogen or methyl, and R$^2$ and R$^3$ are methyl.

5. The compound of claim 1 selected from the group consisting of:
6-[(1-cycloheptyl-4,4-dimethyl-5-oxopyrrolidin-3-yl)methoxy]nicotinonitrile;
4-(4-{[(5-cyanopyridin-2-yl)oxy]methyl}-3,3-dimethyl-2-oxopyrrolidin-1-yl)azepane-1-carboxamide;

1-cycloheptyl-3,3-dimethyl-4-(phenoxymethyl)pyrrolidin-2-one;

1-cycloheptyl-4-{[(2-fluorophenyl)(methyl)amino]methyl}-3,3-dimethylpyrrolidin-2-one;

6-{[1-(-(5-hydroxycyclooctyl)- 4,4-dimethyl-5-oxopyrrolidin-3-yl]methoxyl}nicotinonitrile;

E-4-(4-{[(5-cyanopyridin-2-yl)oxy]methyl}-3,3-dimethyl-2-oxopyrrolidin-1-yl)adamantane-1-carboxamide;

9-(4-{[(5-cyanopyridin-2-yl)oxy]methyl }-3,3-dimethyl-2-oxopyrrolidin-1-yl)bicyclo[3.3.1]nonane-3-carboxamide;

trans ethyl(1R, 7S)-4-(4-{[(5-cyanopyridin-2-yl)oxy]methyl }-3,3-dimethyl-2-oxopyrrolidin-1-yl)bicyclo[5.1.0]octane-8-carboxylate;

trans ethyl (1S, 7R)- 4-(4-{[(5-cyanopyridin-2-yl)oxy]methyl}-3,3-dimethyl-2-oxopyrrolidin-1-yl)bicyclo[5.1.0]octane-8-carboxylate;

6-{[4,4-dimethyl-1-(-(4-methylbicyclo[2.2.2]oct-1-yl)-5-oxopyrrolidin-3-yl]methoxy }nicotinonitrile;

6-{[1-(5-cyanocyclooctyl)- 4,4-dimethyl-5-oxopyrrolidin-3-yl]methoxy}nicotinonitrile;

E-4-(4-{[(5-cyanopyridin-2-yl)oxy]methyl}-3,3-dimethyl-2-oxopyrrolidin-1-yl)adamantane-1-carbonitrile;

E-4-(3,3-dimethyl-2-oxo-4-{[4-(1H-1,2,4-triazol-1-yl)phenoxy]methyl}pyrrolidin-1-yl)adamantane-1-carboxamide;

E-4-(4-{[4-(1H-imidazol-1-yl)phenoxy]methyl}-3,3-dimethyl-2-oxopyrrolidin-1-yl)adamantane-1-carboxamide;

E-4-[3,3-dimethyl-2-oxo-4-({[5-(trifluoromethyl)pyridin-2-yl]oxy}methyl)pyrrolidin-1-yl]-N'-hydroxyadamantane-1-carboximidamide;

E-4-[3,3-dimethyl-2-oxo-4-({[5-(trifluoromethyl)pyridin-2-yl]oxy}methyl)pyrrolidin-1-yl]adamantane-1-carboxamide; and E-4-[3,3-dimethyl-2-oxo-4-({[5-(trifluoromethyl)pyridin-2-yl]oxy}methyl)pyrrolidin-1-yl]adamantane-1-carboximidamide;

or a pharmaceutically acceptable salt thereof, or a combination thereof.

6. A pharmaceutical composition comprising a therapeutically effective amount of the compound of formula (I) of claim 1 or a pharmaceutically acceptable salt thereof, or a combination thereof; and a pharmaceutically acceptable carrier thereof.

7. The compound of claim 1 wherein the compound of formula I is E-4-(4-{[(5-cyanopyridin-2-yl)oxy]methyl}-3,3-dimethyl-2-oxopyrrolidin-1-yl)adamantane-1-carbonitrile, or E-4-[3,3-dimethyl-2-oxo-4-({[5-(trifluoromethyl)pyridin-2-yl]oxy}methyl)pyrrolidin-1-yl]adamantane-1-carboximidamide; or a pharmaceutically acceptable salt thereof, or a combination thereof.

8. The compound of claim 1 wherein the compound of formula I is E-4-(3,3-dimethyl-2-oxo-4-{[4-(1H-1,2,4-triazol-1-yl)phenoxy]methyl}pyrrolidin-1-yl)adamantane-1-carboxamide, or E-4-(4-{[4-(1H-imidazol-1-yl)phenoxy]methyl}-3,3-dimethyl-2-oxopyrrolidin-1-yl)adamantane-1-carboxamide; or a pharmaceutically acceptable salt thereof, or a combination thereof.

9. The compound of claim 1 wherein the compound of formula I is E-4-[3,3-dimethyl-2-oxo-4-({[5-(trifluoromethyl)pyridin-2-yl]oxy}methyl)pyrrolidin-1-yl]-N'-hydroxyadamantane-1-carboximidamide, or E-4-[3,3-dimethyl-2-oxo-4-({[5-(trifluoromethyl)pyridin-2-yl]oxy}methyl)pyrrolidin-1-yl]adamantane-1-carboxamide; or a pharmaceutically acceptable salt thereof, or a combination thereof.

10. The compound of claim 1, werein the compound of formula I is 6-[(1-cycloheptyl-4,4-dimethyl-5-oxopyrrolidin-3-yl)methoxy]nicotinonitrile; or a pharmaceutically acceptable salt thereof or a combination thereof.

11. The compound of claim 1 wherein the compound of formula I is 4-(4-{[(5-cyanopyridin-2-yl)oxy]methyl}-3,3-dimethyl-2-oxopyrrolidin-1-yl)azepane-1-carboxamide; or a pharmaceutically acceptable salt thereof, or a combination thereof.

12. The compound of claim 1 wherein the compound of formula I is 1-cycloheptyl-3,3-dimethyl-4-(phenoxymethyl)pyrrolidin-2-one; or a pharmaceutically acceptable salt thereof, or a combination thereof.

13. The compound of claim 1 wherein the compound of formula I is 1-cycloheptyl-4-{[(2-fluorophenyl)(methyl)amino]methyl}-3,3-dimethylpyrrolidin-2-one; or a pharmaceutically acceptable salt thereof, or a combination thereof.

14. The compound of claim 1 wherein the compound of formula I is 6-{[1-(5-hydroxycyclooctyl)-4,4-dimethyl-5-oxopyrrolidin-3-yl]methoxy}nicotinonitrile; or a pharmaceutically acceptable salt thereof, or a combination thereof.

15. The compound of claim 1 wherein the compound of formula I is E-4-(4-{[(5-cyanopyridin-2-yl)oxy]methyl}-3,3-dimethyl-2-oxopyrrolidin-1-yl)adamantane-1-carboxamide; or a pharmaceutically acceptable salt thereof, or a combination thereof.

16. The compound of claim 1 wherein the compound of formula I is 9-(4-{[(5-cyanopyridin-2-yl)oxy]methyl}-3,3-dimethyl-2-oxopyrrolidin-1-yl)bicyclo[3.3.1]nonane-3-carboxamide; or a pharmaceutically acceptable salt thereof, or a combination thereof.

17. The compound of claim 1 wherein the compound of formula I is trans ethyl (1R,7S)-4-(4-{[(5-cyanopyridin-2-yl)oxy]methyl}-3,3-dimethyl-2-oxopyrrolidin-1-yl)bicyclo[5.1.0]octane-8-carboxylate; or a pharmaceutically acceptable salt thereof, or a combination thereof.

18. The compound of claim 1 wherein the compound of formula I is trans ethyl (1S,7R)-4-(4-{[(5-cyanopyridin-2-yl)oxy]methyl}-3,3-dimethyl-2-oxopyrrolidin-1-yl)bicyclo[5.1.0]octane-8-carboxylate; or a pharmaceutically acceptable salt there of, or a combination thereof.

19. The compound of claim 1 wherein the compound of formula I is 6-{[4,4-dimethyl-1-(4-methylbicyclo[2.2.2]oct-1-yl)-5-oxopyrrolidin-3-yl]methoxy}nicotinonitrile; or a pharmaceutically acceptable salt thereof, or a combination thereof.

20. The compound of claim 1 wherein the compound of formula I is 6-{[1-(5-cyanocyclooctyl)-4,4-dimethyl-5-oxopyrrolidin-3-yl]methoxy}nicotinonitrile; or a pharmaceutically acceptable salt thereof, or a combination thereof.

* * * * *